United States Patent
Nuru et al.

(10) Patent No.: US 11,969,591 B2
(45) Date of Patent: Apr. 30, 2024

(54) TOOLS FOR PACEMAKER LEAD IMPLANTATION

(71) Applicant: TEXAS HEART INSTITUTE, Houston, TX (US)

(72) Inventors: Maryam Nuru, Louisville, KY (US); Ronit Kar, Lexington, KY (US); Mathews Medayil John, Houston, TX (US); Allison Davis Post, Houston, TX (US); Skylar Jobe Buchan, Houston, TX (US); Mehdi Razavi, Houston, TX (US)

(73) Assignee: Texas Heart Institute, Houston, TX (US)

( * ) Notice: Subject to any disclaimer, the term of this patent is extended or adjusted under 35 U.S.C. 154(b) by 230 days.

(21) Appl. No.: 17/513,639

(22) Filed: Oct. 28, 2021

(65) Prior Publication Data

US 2022/0134089 A1    May 5, 2022

Related U.S. Application Data

(60) Provisional application No. 63/107,341, filed on Oct. 29, 2020.

(51) Int. Cl.
| | |
|---|---|
| *A61N 1/05* | (2006.01) |
| *A61B 17/34* | (2006.01) |
| *A61N 1/362* | (2006.01) |
| *A61B 17/00* | (2006.01) |

(52) U.S. Cl.
CPC .......... *A61N 1/057* (2013.01); *A61B 17/3468* (2013.01); *A61N 1/362* (2013.01); *A61B 2017/0042* (2013.01); *A61N 2001/058* (2013.01)

(58) Field of Classification Search
CPC .... A61B 17/3468; A61N 1/362; A61N 1/056; A61N 2001/058
See application file for complete search history.

(56) References Cited

U.S. PATENT DOCUMENTS

| | | | | |
|---|---|---|---|---|
| 2014/0165738 A1* | 6/2014 | Mercer | ............... | G01M 99/007 73/834 |
| 2016/0303367 A1* | 10/2016 | Foster | ................... | A61N 1/057 |

* cited by examiner

*Primary Examiner* — Majid Jamialahmadi
(74) *Attorney, Agent, or Firm* — Conley Rose, P.C.

(57) ABSTRACT

An Example tool for implanting a pacemaker lead includes a body that includes a recess, a first electrical contact positioned within the recess, and a projection coupled to the body. In addition, the tool includes a second electrical contact positioned on the projection. The recess is configured to receive the pacemaker lead therein such that a first electrode of the pacemaker lead is to engage with the first electrical contact and a second electrode of the pacemaker lead is to engage with the second electrical contact. A rotation of the tool about a central axis of the pacemaker lead is configured to rotate the first electrical contact and the first electrode together about the central axis and to slidingly engage the second electrical contact along the second electrode.

16 Claims, 17 Drawing Sheets

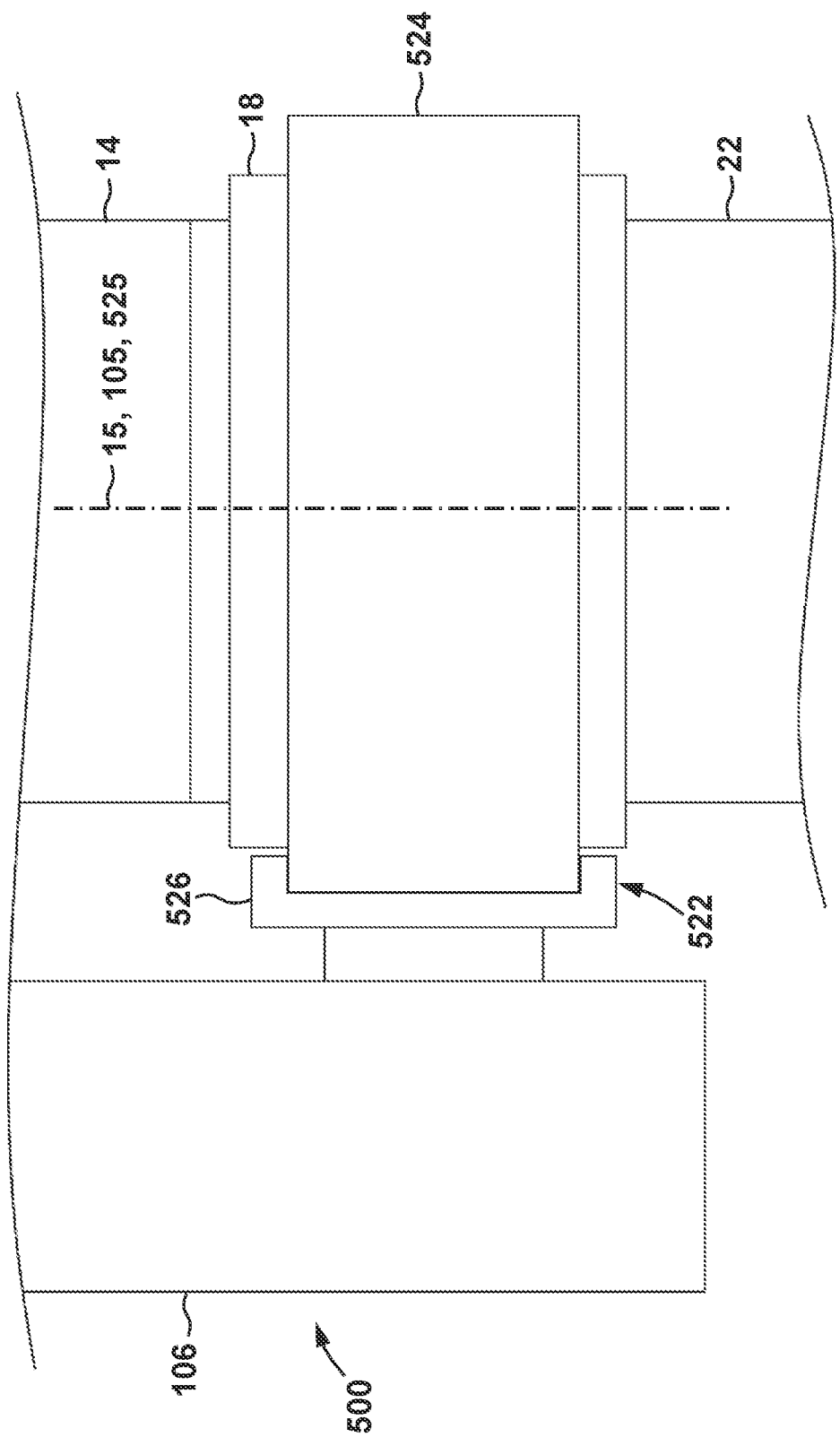

TOOLS FOR PACEMAKER LEAD IMPLANTATION

CROSS-REFERENCE TO RELATED APPLICATIONS

This application claims the benefit of U.S. Provisional Patent Application No. 63/107,341 filed Oct. 29, 2020, and entitled "Tools For Pacemaker Lead Implantation," which is incorporated herein by reference in its entirety.

STATEMENT REGARDING FEDERALLY SPONSORED RESEARCH OR DEVELOPMENT

Not applicable.

BACKGROUND

During cardiac pacemaker implantation, wires called pacemaker leads (or more simply "leads") are inserted into the heart through a minimally invasive procedure. Specifically, the leads are traversed through the vascular system into specific locations in the heart to deliver appropriate electrical pacing therapy. A lead may include an anchoring structure at a distal end thereof that is secured within the myocardium (or other tissue) at the desired location within the heart. Proper insertion of the anchoring structure ensures that the lead is properly secured to the myocardium; however, over insertion may cause unnecessary damage to the tissue of the heart.

BRIEF SUMMARY

Some embodiments described herein are directed to a tool for implanting a pacemaker lead. In some embodiments, the tool includes a body that includes a recess, a first electrical contact positioned within the recess, a projection coupled to the body, and a second electrical contact positioned on the projection. The recess is configured to receive the pacemaker lead therein such that a first electrode of the pacemaker lead is to engage with the first electrical contact and a second electrode of the pacemaker lead is to engage with the second electrical contact. A rotation of the tool about a central axis of the pacemaker lead is configured to rotate the first electrical contact and the first electrode together about the central axis and to slidingly engage the second electrical contact along the second electrode.

Some embodiments described herein are directed to a tool for implanting a pacemaker lead. The pacemaker lead includes a proximal end and a distal end, a tip electrode at the proximal end, a ring electrode at the proximal end, and an anchoring structure at the distal end. In some embodiments, the tool includes a body that includes a central axis and a recess extending radially into the body relative to the central axis. In addition, the tool includes a first electrical contact positioned within the recess. The recess is configured to receive the tip electrode of the pacemaker lead therein such that the tip electrode of the pacemaker lead is to engage with the first electrical contact. Further, the tool includes a projection extending from the body in an axial direction with respect to the central axis. Still further, the tool includes a second electrical contact positioned on the projection. The second electrical contact is configured to engaged with the ring electrode. A rotation of the tool about the central axis is configured to rotate the first electrical contact and the tip electrode together about the central axis and to slidingly engage the second electrical contact along the ring electrode in a circumferential direction about the central axis.

Some embodiments described herein are directed to a tool for implanting a pacemaker lead. In some embodiments, the tool includes a body that includes a central axis and a recess extending radially into the body relative to the central axis. In addition, the tool includes a pair of arms coupled to the body, wherein compression of the arms toward one another is configured to widen the recess. Further, the tool includes a first electrical contact including a notch that is positioned within the recess, a projection coupled to the body, and a second electrical contact positioned on the projection. The recess is configured to receive the pacemaker lead within the notch such that a first electrode of the pacemaker lead is to engage with the first electrical contact and a second electrode of the pacemaker lead is to engage with the second electrical contact. A rotation of the tool about the central axis is configured to rotate the first electrical contact and the first electrode together about the central axis and to rotate the second electrical contact about the second electrode.

Embodiments described herein comprise a combination of features and characteristics intended to address various shortcomings associated with certain prior devices, systems, and methods. The foregoing has outlined rather broadly the features and technical characteristics of the disclosed embodiments in order that the detailed description that follows may be better understood. The various characteristics and features described above, as well as others, will be readily apparent to those skilled in the art upon reading the following detailed description, and by referring to the accompanying drawings. It should be appreciated that the conception and the specific embodiments disclosed may be readily utilized as a basis for modifying or designing other structures for carrying out the same purposes as the disclosed embodiments. It should also be realized that such equivalent constructions do not depart from the spirit and scope of the principles disclosed herein.

BRIEF DESCRIPTION OF THE DRAWINGS

For a detailed description of various exemplary embodiments, reference will now be made to the accompanying drawings in which:

FIG. 17 is a side view of the engagement between a tool for implanting a pacemaker lead and the pacemaker lead of FIG. 2 according to some embodiments.

DETAILED DESCRIPTION

Figure 1:
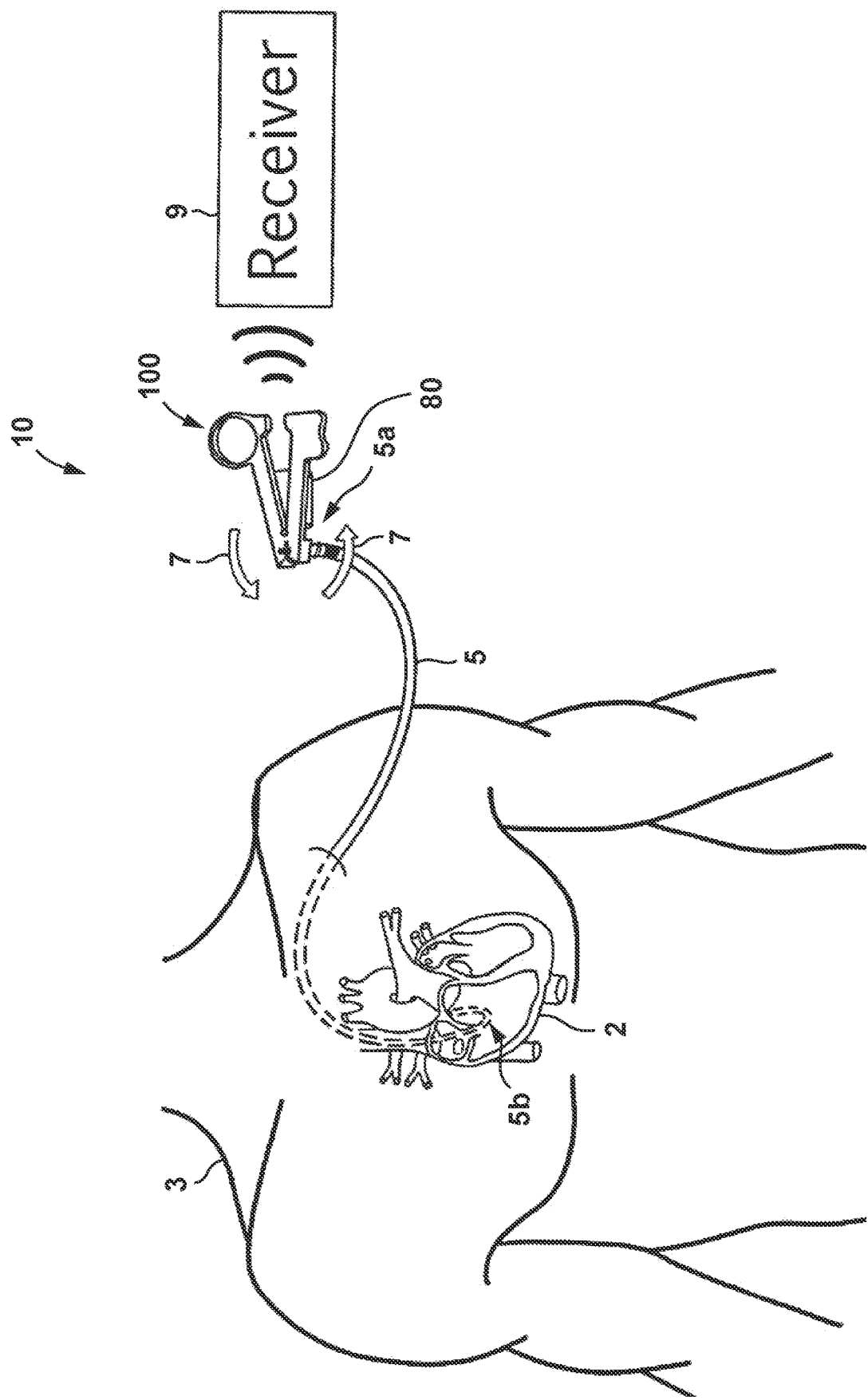
FIG. 1 is a front view of a system for implanting a pacemaker lead according to some embodiments.

The following discussion is directed to various embodiments. However, one of ordinary skill in the art will understand that the examples disclosed herein have broad application, and that the discussion of any embodiment is meant only to be exemplary of that embodiment, and not intended to suggest that the scope of the disclosure, including the claims, is limited to that embodiment.

The drawing figures are not necessarily to scale. Certain features and components herein may be shown exaggerated in scale or in somewhat schematic form and some details of conventional elements may not be shown in interest of clarity and conciseness.

In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection of the two devices, or through an indirect connection that is established via other devices, components, nodes, and connections. In addition, as used herein, the terms "axial" and "axially" generally mean along or parallel to a given axis (e.g., central axis of a body or a port), while the terms "radial" and "radially" generally mean perpendicular to the given axis. For instance, an axial distance refers to a distance measured along or parallel to the axis, and a radial distance means a distance measured perpendicular to the axis. Further, when used herein (including in the claims) in connection with a stated value, the words "about," "generally," "substantially," "approximately," and the like mean within a range of plus or minus 10% of the stated value.

As previously described, proper implantation of the anchoring structure of a pacemaker lead within the myocardium of a patient's heart is essential to ensure that the pacemaker lead is secured in the proper location to emit effective electrical signals during use. However, unnecessary tissue damage may result from an over insertion of the anchoring structure into the target tissue. A lead implantation procedure may be performed with fluoroscopic guidance; however, a physician may also utilize electrical impedance measurements to provide further insight. Without being limited to this or any other theory, blood may have a different electrical impedance than myocardial tissue. Specifically, myocardial tissue may have a higher impedance than blood. As a result, a physician may measure an impedance within the material surrounding the anchoring structure so as to determine when the anchoring structure is sufficiently inserted within the myocardium. In addition, the impedance measurements may also provide an indication of the health of the myocardium (e.g., by providing an indication of the circulation, hydration, and general makeup of the myocardium).

In some specific cases, the anchoring structure of the lead may comprise a helical element that is inserted within the myocardium via rotation. In these circumstances, impedance measurements may be accomplished via electrical coupling (e.g., via alligator clips or other suitable electrical connectors) of electrodes on the proximal end of the lead to a suitable impedance measurement unit. However, the rotation of the lead (or a portion thereof) to further insert the helical anchoring element in the myocardium may result in entanglement of the wires (or other conductors) coupling the proximal end electrodes to the impedance measurement unit. As a result, in many cases, the electrical connectors are removed so as to allow the physician to advance the helical anchoring element within the myocardium (e.g., via rotation as previously described), and then are re-connected to the proximal-end electrodes of the lead to determine the resulting impedance measurement. However, this process is cumbersome and increases the overall time of the procedure. In addition, determination of an over-insertion (e.g., via the impedance measurements) may be delayed as a result of repeated disconnection of the electrical connectors.

Accordingly, embodiments disclosed herein include tools for pacemaker lead implantation that may allow for constant (or substantially constant) electrical connection with the proximal-end electrodes of the lead as the anchoring structure of the lead is embedded into the myocardium (or other tissue). Specifically, embodiments disclosed herein may allow for constant (or substantially constant) electrical coupling of the proximal-end electrodes of the lead to a suitable impedance measurement unit during rotation of the lead to advance a helical anchoring structure within the corresponding tissue as previously described.

For example, FIG. 1 depicts a system 10 for implanting a pacemaker lead 5 into the tissue of the heart 2 of a patient 3. In some embodiments (e.g., such as in the embodiment of FIG. 1), the system 10 may be configured for inserting a distal end 5b of the lead 5 into the His bundle of the heart 2 (however, other insertion locations within the heart 2 are contemplated for other, various embodiments). More specifically, in this embodiment, the pacing lead 5 is inserted through the subclavian vein and superior vena cava, into the right atrium. From there, the distal end 5b of the lead 5 is passed through the tricuspid valve and is lodged into the bundle of His. As will be described in more detail below, the insertion of the distal end 5a of lead 5 within the bundle of His (or other target tissue) may be accomplished by rotating the lead 5 about a central or longitudinal axis thereof (e.g., as generally indicated by the block arrow 7 shown in FIG. 1).

System 10 also includes a pacemaker lead implantation tool 100, which may be more simply referred to herein as "tool 100." Tool 100 is coupled to the proximal end 5a of the lead 5, and may be gripped by the physician so as to allow for the insertion and manipulation of the lead 5 during the lead implantation procedure generally described above. In addition, as will be described in more detail below, the tool 100 may also maintain electrical contact between one or more electrodes disposed on the lead 5 so as to enable impedance measurement during the lead implantation procedure.

In particular, tool 100 may include an electronics hub 80 that is communicatively coupled to the electrodes (not shown in FIG. 1) on the lead 5. In some embodiments, the electronics hub 80 may be configured to receive the electrical signal(s) from the lead electrodes and determine (e.g., calculate) an impedance based thereon. In some embodiments (e.g., such as in the embodiment shown in FIG. 1), the electronics hub 80 is also communicatively coupled to a receiver 9. The electronics hub 80 may be wirelessly coupled to the receiver 9 as shown in FIG. 1 or may be coupled to the receiver 9 via a wired connection. During operations, the electronics hub 80 may determine an impedance between one or more electrodes on the lead 5 and then communicate the impedance values to the receiver 9. The receiver 9 may include an electronic display (e.g., liquid crystal display (LCD), organic light emitting diode (OLED) display, plasma display, etc.), and/or any other suitable mechanism or system for communicating visual information (e.g., indicator lights). In some embodiments, a physician (or other individual) may receive information (e.g., visual information, audible information, a combination thereof) from the receiver 9 that is indicative of the impedance values determined by the electronics hub 80 (e.g., the impedance values themselves, an alarm based on the impedance values, or any other inference or conclusion that may be drawn from the raw impedance values). In some embodiments, the electronics hub 80 may provide other parameters related to the received or sensed electrical signals (e.g., current, voltage, etc.) to the receiver 9 so that the receiver 9 may perform the impedance calculations. Further details of the tool 100 are provided below. However, a description will first be provided for an example of the lead 5 that may be utilized during the implantation procedure depicted in FIG. 1.

Figure 2:
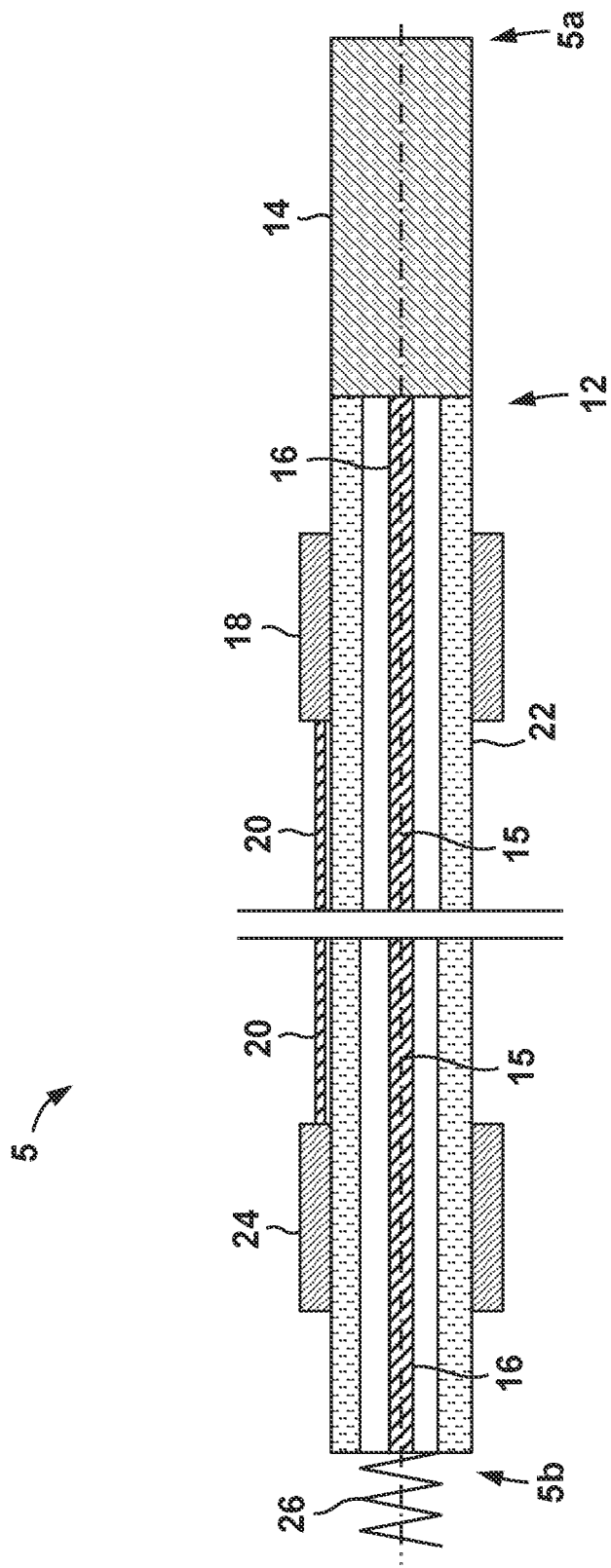
FIG. 2 is a side cross-sectional view of a pacemaker lead.

Specifically, referring now to FIG. 2, a schematic cross-section of lead 5 is shown. Lead 5 includes a central or longitudinal axis 15 that extends between proximal end 5a and distal end 5b. In addition, lead 5 includes an anchoring structure 26 at distal end 5b and a connector 12 at proximal end 5a.

The anchoring structure 26 may comprise a variety of different designs. In some embodiments (e.g., such as in the embodiment of FIG. 2), the anchoring structure 26 may comprise a helical screw that may be configured to pierce the heart tissue (e.g., the myocardium) of the patient 3 (FIG. 1). In particular, when anchoring structure 26 are rotated about axis 15 in a first direction, the anchoring structure 26 may advance axially into the target tissue, and when anchoring structure 26 is rotated about axis 15 in a second, opposite direction, the anchoring structure 26 may be axially withdrawn from the target tissue.

The connector 12 may comprise any suitable connector such as, for instance, an IS-1 type connector, an IS-4 type connector, etc. Generally speaking, the connector 12 includes a first electrode 14 at proximal end 5a, and at least one second electrode 18 axially spaced (e.g., along axis 15) from the proximal end 5a and first electrode 14. Because the first electrode 14 is disposed at the proximal end 5a of the lead 5, it may be referred to herein as a "tip electrode." The second electrode 18 may comprise a so-called "ring electrode" that extends circumferentially about axis 15.

A central conductor 16 extends axially from the first electrode 14 to the anchoring structure 26 so that first electrode 14 and anchoring structure 26 are electrically coupled to one another via the central conductor 16. In addition, a second conductor 20 extends from the second electrode to a third electrode 24 that is proximate the distal end 5b but is axially spaced from the anchoring structure 26.

The third electrode 24 may also comprise a ring electrode that extends circumferentially about axis 15. Thus, the second electrode 18 and third electrode 24 are electrically coupled to one another via the second conductor 20. A dielectric sleeve or sheath 22 is wrapped about the central conductor 16 and generally extends axially from the first electrode 14 to the anchoring structure 26. Thus, the electrodes 18, 24 are generally electrically insulated from the anchoring structure 26 and first electrode 14 via the sheath 22.

During operations, an electrical current may be provided to one or both of the electrodes 14, 18, and is therefore conducted to the anchoring structure 26, and third electrode 24, respectively, via the conductors 16, 20, respectively. Within the body of the patient 3 (FIG. 1), the distal end 5b of lead 5 may be surrounded by fluid and/or tissue that may conduct the current between the electrode 24 and the anchoring structure 26, such that the current is ultimately conducted back to the electrodes 14, 18 via conductors 16, 20, respectively. As a result, a voltage difference that is measured or detected between the electrodes 14, 18 for a known injected electrical current may be used to calculate (or otherwise determine) the impedance of the fluid/tissue that conducted the electrical current between the electrode 24 and anchoring structure 26. Alternatively, a current may be measured between the electrodes 14, 18 for a known induced voltage differential that may also be used to calculate (or otherwise determine) the impedance of the fluid/tissue that conducted the resulting electric current between the electrode 24 and anchoring structure 26. Because tissue (e.g., such the myocardium) has a higher impedance than bodily fluids, such as blood, when the anchoring structure 26 is inserted within the tissue of the heart, one would expect to see the impedance between the two electrodes 14, 18 to increase. Because the impedance calculated between the electrodes 14, 18 may also include the impedance contributed by the electrodes 14, 18, 24, conductors 16, 20, and anchoring structure 26, one may consider how the impedance values are changing over time rather than focusing on instantaneous impedance values.

Referring briefly now to FIGS. 1 and 2, during these operations, the connector 12 of the lead 5 may be engaged with tool 100. As will be described in more detail below, tool 100 may include one or more electrical contacts (e.g., electrical contacts 120, 122 described below) that are to engage with the electrodes 14, 18 on lead 5 so as to electrically coupled electrodes 14, 18 to electronics hub 80 and therefore facilitate the impedance measurements previously described above. The engagement of the electrical contacts on the tool 100 and the electrodes 14, 18 on the lead 5 may be maintained even during rotation of the lead 5 to insert the anchoring structure 26 within the target tissue as previously described above.

Figure 3:
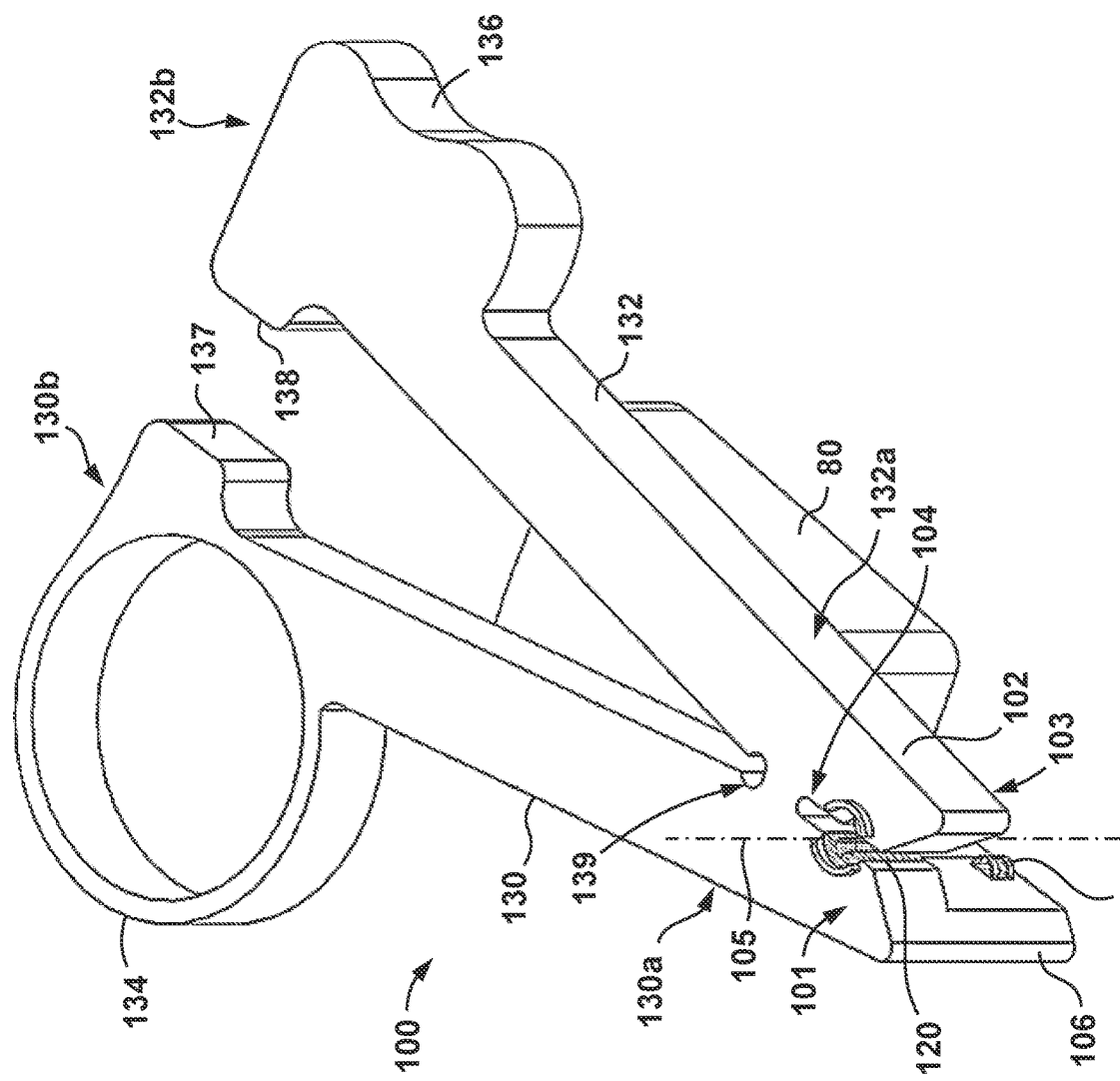
FIG. 3 is a perspective view of a tool for implanting a pacemaker lead according to some embodiments.

Referring now to FIG. 3, the tool 100 includes a body 102 defining a recess 104 therein. In addition, tool 100 includes a pair of arms 130, 132 coupled to and extending outward from body 102.

Figure 4:
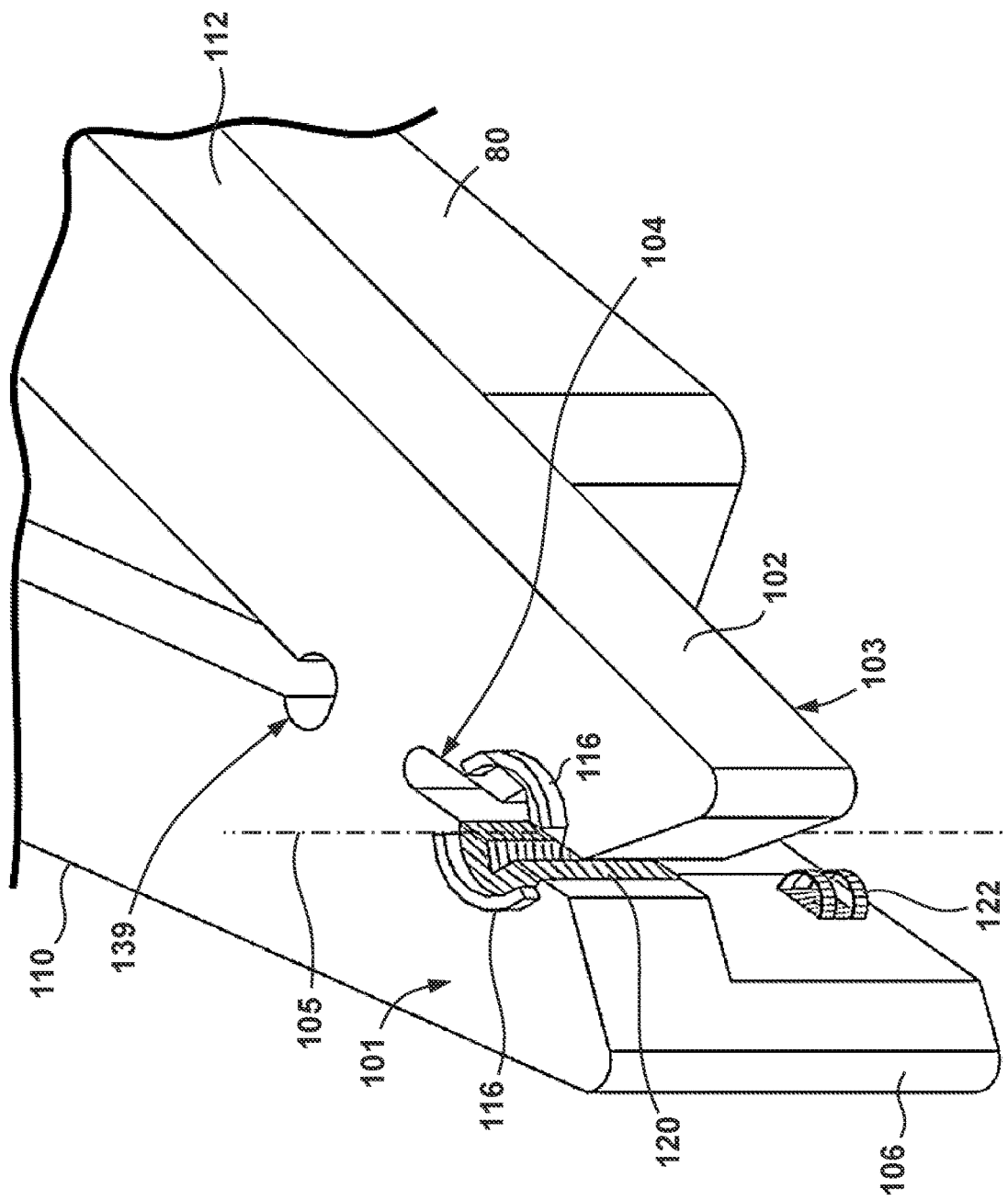
FIG. 4 is an enlarged perspective view of a portion of the body of the tool of FIG. 3 according to some embodiments.

Referring now to FIG. 4, body 102 includes a central axis 105, a top side 101, and a bottom side 103 axially opposite the top side 101. The recess 104 extends into body 102 in a radial direction relative to axis 105. In addition, recess 104 also extends axially between the top side 101 and bottom side 103. A projection 106 extends axially from bottom side 103.

Figure 5:
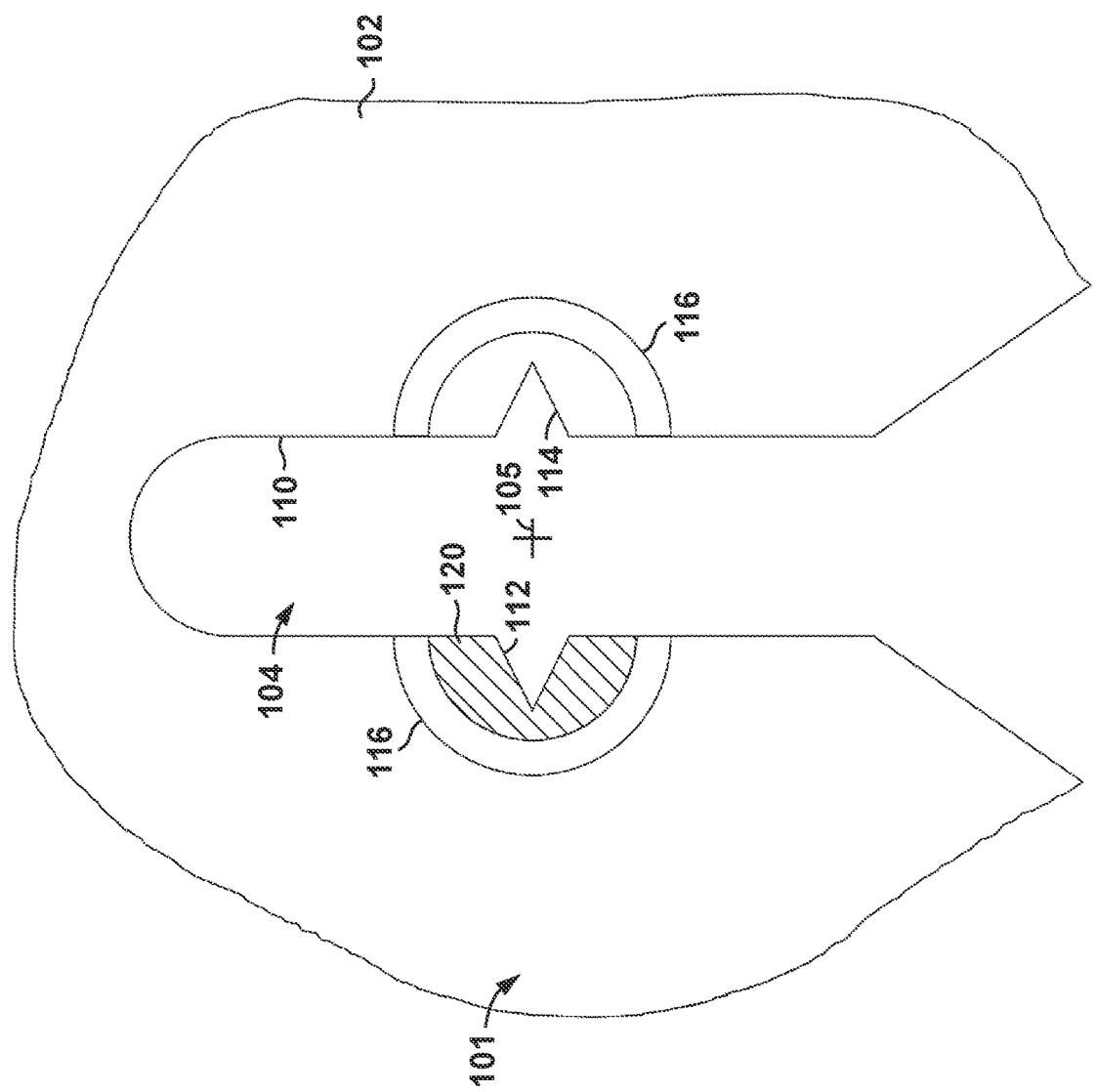
FIG. 5 is a top view of a recess form in the body of the tool of FIG. 3 according to some embodiments.

Referring briefly to FIG. 5, recess 104 includes an inner wall 110. A pair of notches 112, 114 is formed on inner wall 110 such that the notches 112, 114 are disposed on radially opposite sides from axis 105 (i.e., the notches 112, 114 are disposed about 180° from one another about axis 105). The notches 112, 114 are generally V-shaped; however, other shapes are contemplated in other embodiments (e.g., cylindrical, rectangular, square, etc.). In addition, a pair of arcuate guide walls 116 project axially upward from upper side 101 of body 102. The guide walls 116 extend about the notches 112, 114. During operations, the guide walls 116 may provide a visual indication for aligning the lead 5 (or a portion thereof) with the notches 112, 114 within the recess 104.

A first electrical contact 120 is positioned within the recess 104. In particular, the first electrical contact 120 is embedded within and thus incorporated within the inner wall 110. In some embodiments, first electrode 120 forms the notch 112. In some embodiments, the first electrical contact 120 may be mounted to and thus project outward from the inner wall 110.

Referring again to FIG. 4, a second electrical contact 122 is positioned on the projection 106. Thus, the electrical contacts 120, 122 are spaced from one another along the axis 105. The second electrical contact 122 extends outward from the projection 106 in a generally perpendicular (or radial) direction to axis 105. In some embodiments, the second electrical contact 122 may extend radially toward axis 105. In some embodiments, the second electrical contact 122 may be biased outward from projection 106. For instance, as shown in FIG. 4, in some embodiments, the second electrical contact 122 may comprise a flat spring (e.g., leaf spring) that is bent or curved so as to project outward or away from projection 106. In some embodiments, second electrical contact 122 may be biased outward from projection 106 via a coiled spring or other suitable biasing member.

Generally speaking, the electrical contacts 120, 122 may comprise an electrically conducting material. For instance, in some embodiments, the electrical contacts 120, 122 may comprise gold, copper, titanium, brass, silver, platinum, platinum-iridium, stainless steel, or combinations and/or alloys thereof.

Referring again to FIG. 3, the arms 130, 132 extend outward from body 102 in a generally radial direction with respect to axis 105. Arms 130, 132 may include a first or inner end 130a, 132a, respectively, that are engaged with body 102 and a second or outer end 130b, 132b that are spaced from body 102. Arms 130, 132 may generally diverge from one another when moving from inner ends 130a, 132a at body 102 toward outer ends 130b, 132b. Outer ends 130b, 132b may include gripping structures that are configured to facilitate manipulation of the arms 130, 132 during use. In particular, outer end 130b of the arm 130 may include a ring 134 and outer end 132b of arm 132 may include a contoured tab 136. In some embodiments, the ring 134 may be configured to receive a thumb of a user (not shown), while the tab 136 may be engaged with an index (or other) finger of the user. In addition, the outer ends 130b, 132b of arms 130, 132 may include stoppers 137, 138, respectively, that generally face one another.

Together, the arms 130, 132 and the body 102 may be integrated into a single-piece, monolithic body. Accordingly, the inner ends 130a, 132a of arms 130, 132 may be integrally engaged with body 102. In some embodiments, the body 102, projection 106, and arms 130, 132 may be integrally formed together via a molding process (e.g., injection molding, press molding, etc.). In some embodiments, body 102, projection 106, and arms 130, 132 may be formed of a relatively compliant material (e.g., such as a polymer, carbon fiber, resin, an elastomer, a metal, etc.), so as to allow for elastic deformation during operations. In some embodiments, the body 102, projection 106, and arms 130, 132 may be formed from polyethylene and/or another plastic or polymer material. In some embodiments, the body 102, projection 106, and arms 130, 132 may be formed from a metal, thermoplastic, an elastomer (e.g., natural or synthetic rubber), etc.

During operations, a user (e.g., a physician) may compress the arms 130, 132 toward one another. In particular, the user may grasp the arms 130, 132 via the gripping structures (e.g., ring 134 and tab 136) as described above and compress the outer ends 130b, 132b toward one another. Because the inner ends 130a, 132a of arms 130, 132 are engaged with body 102 (and may be monolithically formed with body 102 as described above), as the outer ends 130b, 132b of arms 130, 132 are compressed toward one another, the recess 104 of body 102 may be generally widened or split apart along a plane that is perpendicular to the axis 105. The compression of the outer ends 130a, 132b may be limited by engagement of the stoppers 137, 138. The arms 130, 132 may be mounted to the body 102 (and formed of a suitably compliant material) so that the outer ends 130b, 132b of arms 130, 132 are generally biased apart from one another. Thus, when the compressive force is removed from the outer ends 130b, 132b, the arms 130, 132 may generally move away from one another thus closing or narrowing the recess 104.

An arcuate recess 139 is formed at the intersection of the inner ends 130a, 132a of arms 130, 132 and body 102. Without being limited to this or any other theory, the recess 139 may be configured to relieve stresses (e.g., by dissipating a stress concentration) in the body 102 and arms 130, 132 during movement of the arms 130, 132 toward and away from one another. In various embodiments, the recess 139 may be circular, oval, or any other suitable arcuate shape.

In some embodiments, the electronics hub 80 may be mounted to a single one of the arms 130, 132. Without being limited to this or any other theory, by mounting the electronics hub 80 to one of the arms 130, 132, the electronics hub 80 may avoid interfering with the relative movement of the arms 130, 132 during operations.

Figure 6:
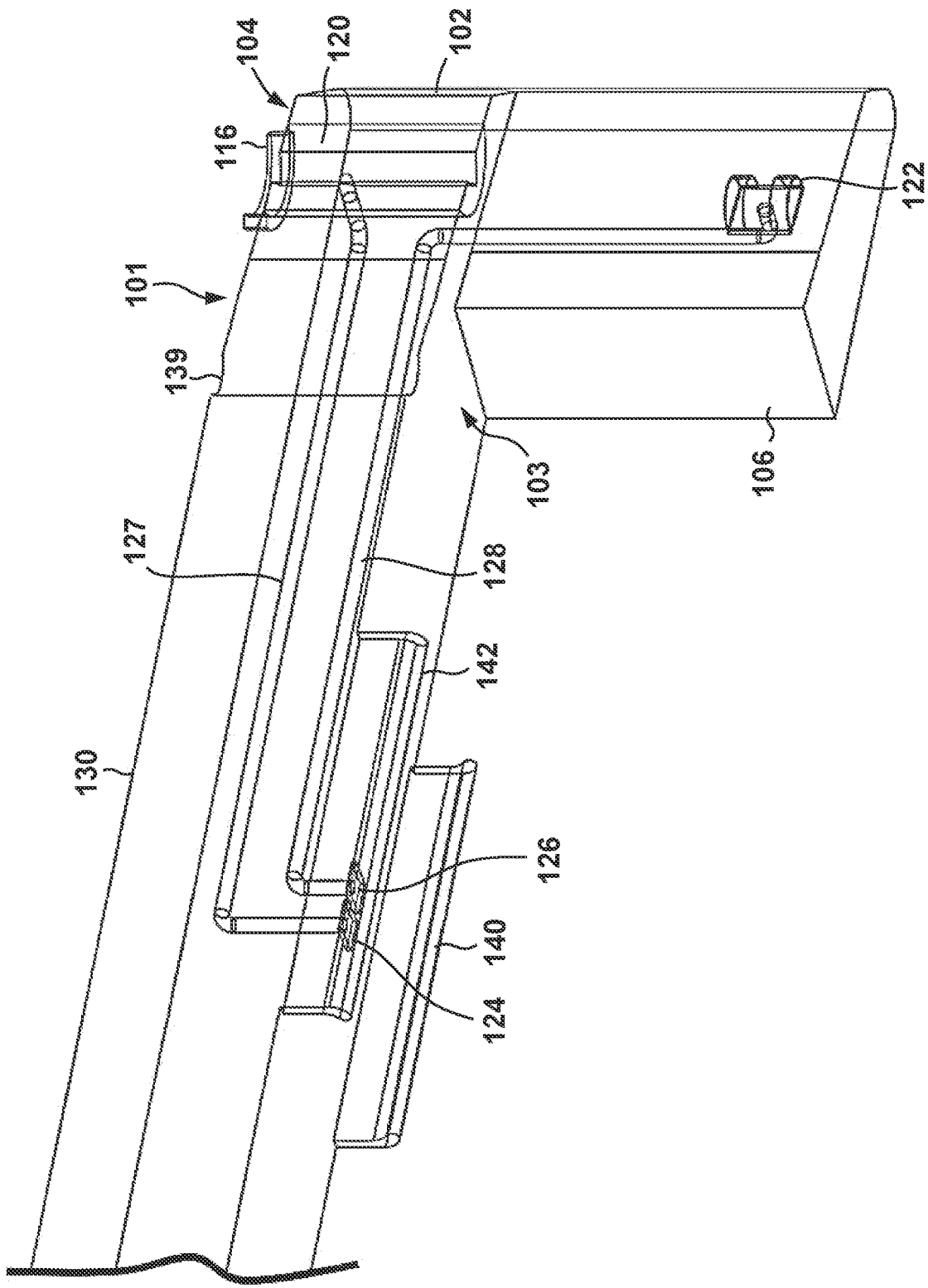
FIG. 6 is a perspective, cross-sectional view of the tool of FIG. 3 according to some embodiments.
Figure 7:
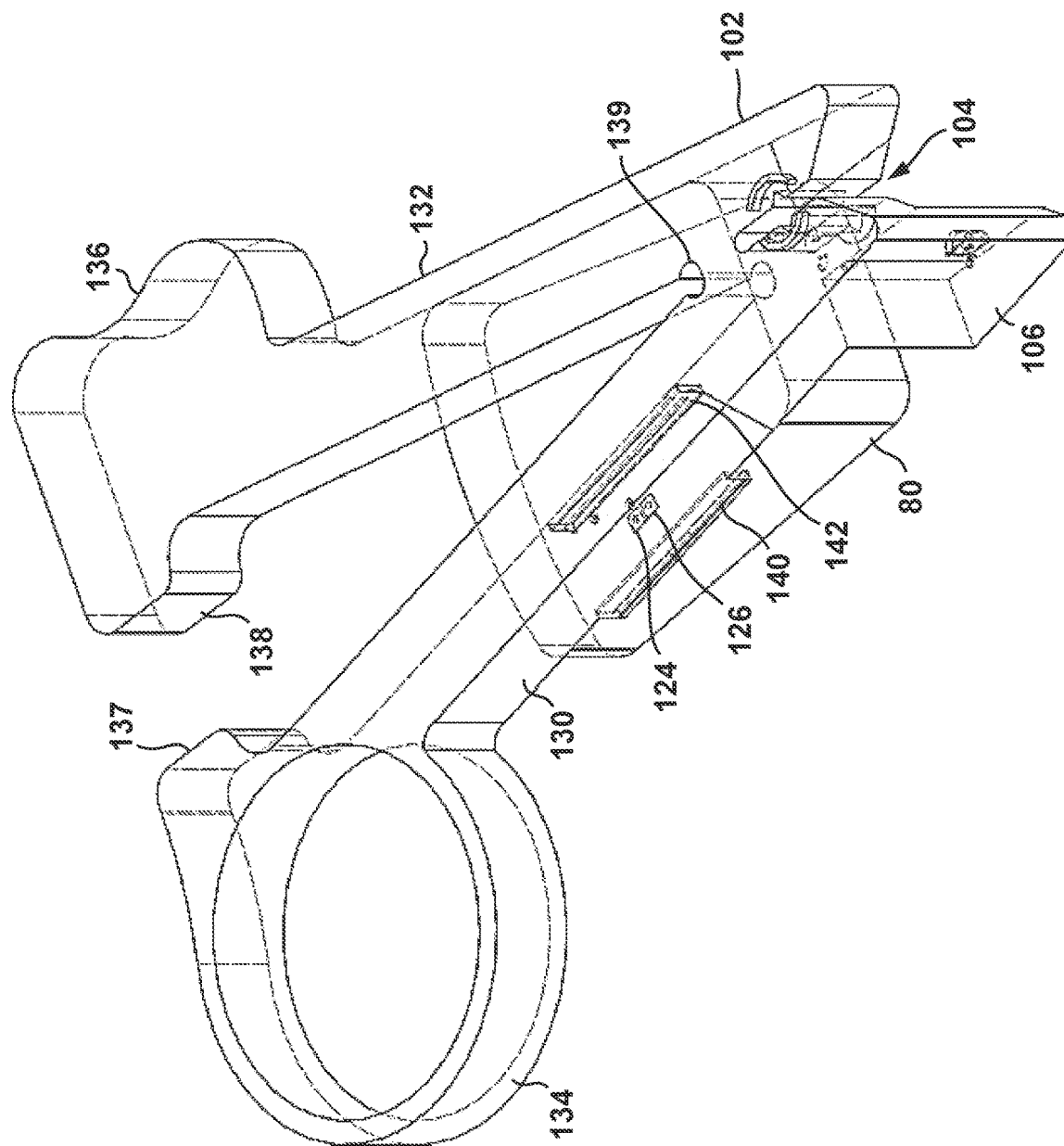
FIG. 7 is a perspective view of the tool of FIG. 3 wherein the tool is shown as a perspective, transparent wireframe to depict an electronics hub according coupled thereto to some embodiments.

In the embodiment of FIG. 3, the electronics hub 80 is mounted to the arm 130. More particularly, referring now to FIGS. 6 and 7, the arm 130 may include a pair of mounting rails 140, 142. In addition, conductive contacts 124, 126 are disposed on arm 130 on a side adjacent to the bottom side 103 of body 102. As shown in FIG. 6, the conductive contacts 124, 126 are electrically coupled to the electrical contacts 120, 122, respectively, via suitable conductors 127, 128, respectively, that are routed within the body 102 and arm 130. In some embodiments, the conductors 127, 128 may be partially or entirely external to body 102 and/or arm 130. In some embodiments, the conductors 127, 128 may be routed through channels or grooves in the body 102 and/or arm 130. The conductive contacts 124, 126 may comprise any suitable conductive material (e.g., such any one or more of the conductive materials listed above for electrical contacts 120, 122). In addition, the conductors 127, 128 may comprise wires, or any other suitable electrical conductors.

Figure 8:
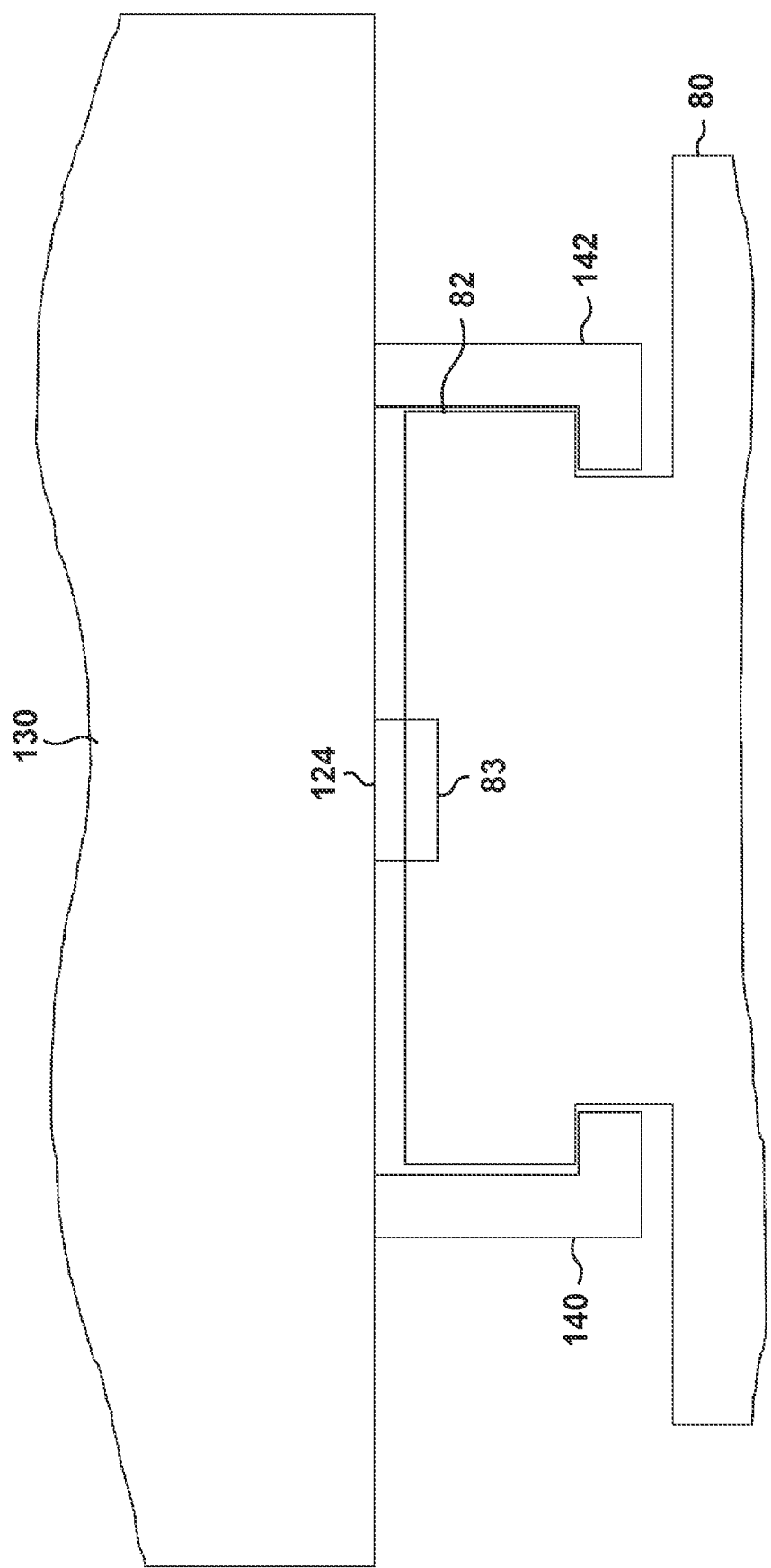
FIG. 8 is a front view of an engagement between the electronics hub and an arm of the tool of FIG. 3 according to some embodiments.

Referring now to FIG. 8, electronics hub 80 may be engaged with the mounting rails 140, 142 on arm 130. In particular, electronics hub 80 may include a suitable projection or other structure 82 that is configured to mate with the rails 140, 142 so that the electronics hub 80 may be suspended from arm 130 during operations. In the embodiment of FIG. 8, the structure 82 comprises a projection that is inserted (e.g., slid) between the mounting rails 140, 142.

In some embodiments, the mounting structure 82 may comprise recesses (not shown) in the electronics hub 80 that receive the mounting rails 140, 142 therein. Regardless, the mounting structure 82 (or another surface on electronic hub 80) may include corresponding electrical contacts 83 that are to engage with the electrical contacts 124, 126 so as to electrically couple the electrical contacts 120, 122 to the components disposed within electronics hub 80 (described below), via contacts 124, 126 and conductors 127, 128, respectively. In the view of FIG. 8, only one of the electrical contacts 83 is shown engaging with the electrical contact 124 because the other electrical contact 126 and the corresponding electrical contact 83 on electronics hub 80 are occluded.

Additionally, in some embodiments, the electronics hub 80 may be mounted to both of the arms 130, 132. Further, in some embodiments, the electronics hub 80 may be integrally formed (and thus not readily removable) from the body 102 and/or arms 130, 132. Still further, in some embodiments, the electronics hub 80 may be coupled to the tool 100 (or a portion or part thereof) with adhesive, magnets, or any other suitable manner.

Figure 9:
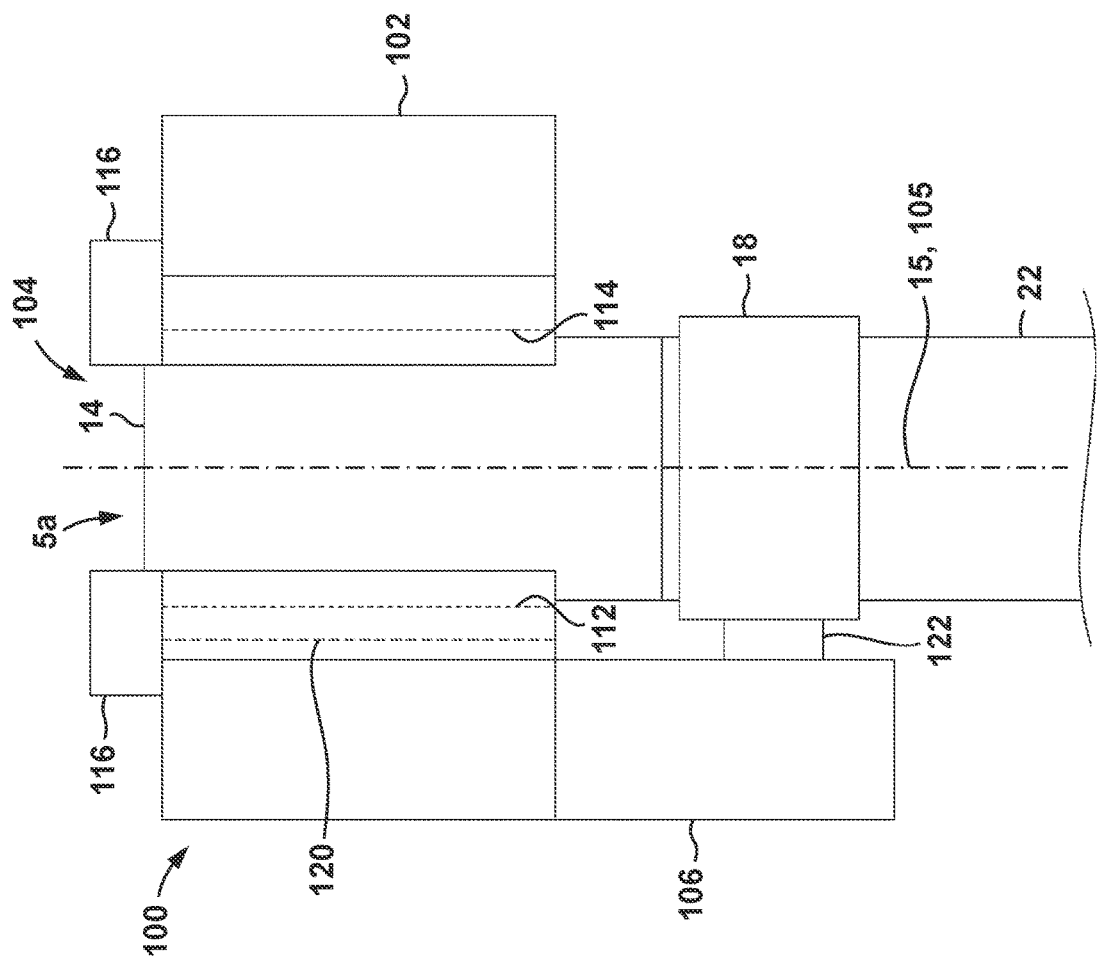
FIG. 9 is a side view of the engagement between the tool of FIG. 3 and the pacemaker lead of FIG. 2 according to some embodiments.

Referring now to FIGS. 2, 3, and 9, during a pacemaker lead implantation procedure, the connector 12 of lead 5 may be engaged with the body 102 of tool 100. In particular, the first electrode 14 of lead 5 may be inserted within the recess 104 (e.g., in a generally radial direction with respect to axis 105) so that the electrode 14 is received within the notches 112, 114 and therefore engaged with first electrical contact 120. To allow the insertion of electrode 14 within the recess 104, the arms 130, 132 may be compressed together so as to widen the recess 104 as generally described above. Once the electrode 14 is fully inserted within the recess 104, the arms 130, 132 maybe released so as to allow the recess 104 to close around the electrode 14 thereby capturing the electrode 14 within the notches 112, 114. When the electrode 14 of lead 5 is inserted within recess 104 in this manner, the axis 15 of lead 5 may be generally aligned with (or may be at least parallel to) the axis 105 of recess 104 at the proximal end 5a. In addition, when the first electrode 14 of lead 5 is inserted within recess 104, the second electrical contact 122 on projection 106 may be biased into engagement with the second electrode 18. Specifically, the engagement between the second electrode 18 and the second electrical contact 122 may deflect or elastically deform the second electrical contact 122.

During operations, the tool 100 may be rotated about the aligned axes 15, 105 which thereby drives rotation of the first electrode 14 about the axis 15 via the engagement of first electrode 14 within recess 104. The rotation of first electrode 14 about axis 15 also results in a corresponding rotation of the central conductor 16 and anchoring structure 26 about the axis 15. The rotation of anchoring structure 26 (e.g., via electrode 14 and conductor 16) may selectively advance or withdrawal the anchoring structure 26 from the myocardium (or other tissue) as previously described. In addition, as the tool 100 and electrode 14 are rotated about the axes 15, 105 as described above, the second electrical contact 122 slides circumferentially along the second electrode 18 so as to maintain electrical contact therewith. Accordingly, during operations, electrical contact may be maintained between the first electrical contact 120 and first electrode 14, and between the second electrical contact 122 and the second electrode 18.

Figure 10:
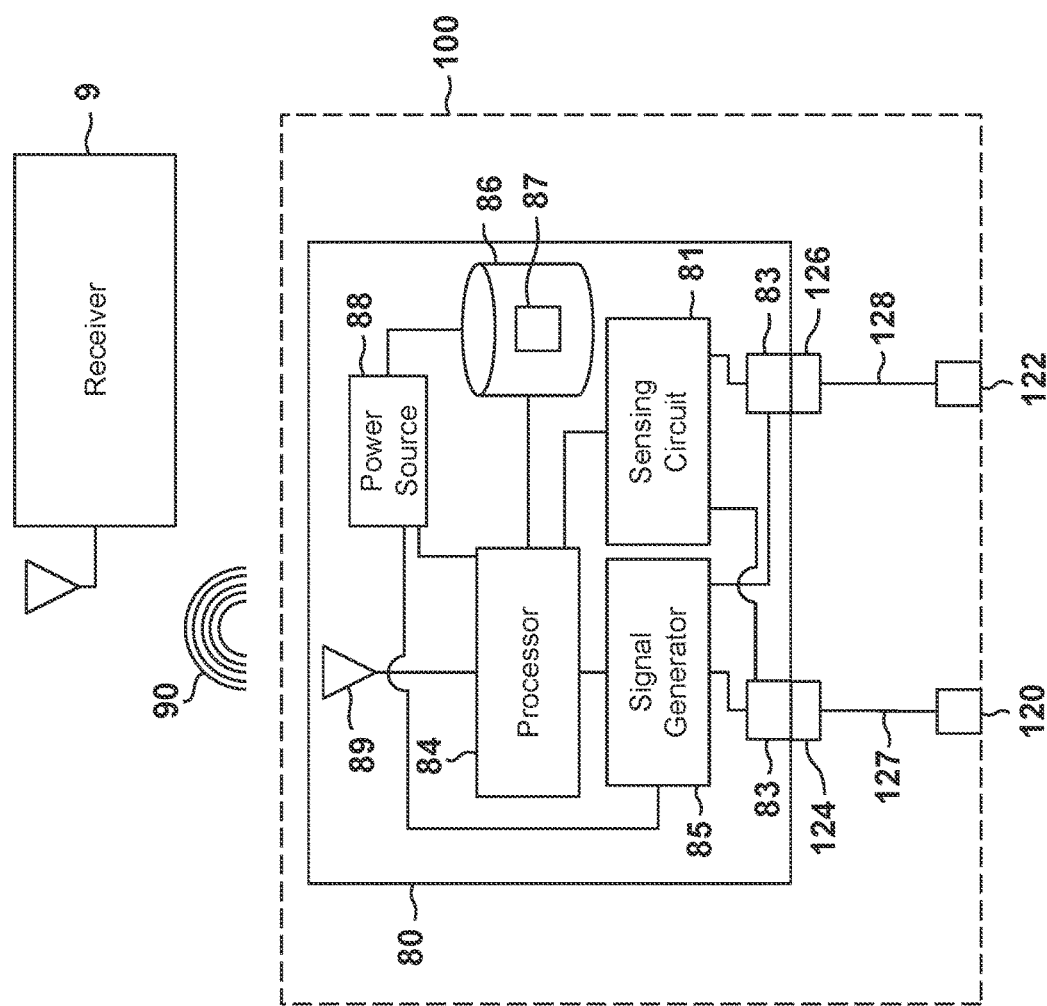
FIG. 10 is a diagram of the tool of FIG. 3 and a receiver of the system in FIG. 1 according to some embodiments.

Referring now to FIG. 10, electronics hub 80 may comprise any suitable electronic components for emitting electric current that is conducted to the electrical contacts 120, 122 and for determining a voltage drop and/or impedance between the electrical contacts 120, 122 as previously described above. For instance, in some embodiments, electronics hub 80 includes a processor 84, a memory 86, a power source 88, a signal generator 85, and a sensing circuit 81.

The processor 84 (e.g., microprocessor, central processing unit (CPU), etc.) executes machine-readable instructions 87 stored on memory 86 (e.g., a non-transitory machine-readable medium), thereby causing the processor 84 (and, more generally, the electronics hub 80) to perform some or all of the actions attributed herein to the processor 84 (and, more generally, to the electronics hub 80). The memory 86 may comprise volatile storage (e.g., random access memory (RAM)), non-volatile storage (e.g., read-only memory (ROM), flash storage, etc.), or combinations of both volatile and non-volatile storage. Data read or written by the processor 84 when executing the machine-readable instructions 87 can also be stored on memory 86.

Power source 88 may comprise any suitable device or system for storing electrical and emitting electric current. In some embodiments, the power source 88 may comprise a battery, however other suitable devices or systems are contemplated herein (e.g., one or more capacitors).

Signal generator 85 may comprise one or more circuits and/or other components that are configured to emit a desired and known electrical current to the electrical contacts 83. For instance, in some embodiments, the signal generator 85 may comprise one or more current mirror circuits (e.g., a Wilson current mirror, a MOSFET current mirror, a Widlar current mirror, etc.) so as to output an electrical current to the electrical contacts 83 that has a desired and known frequency, pulse width, amplitude, amperage, etc. In some embodiments, the electrical current output to the electrical contacts 83 may have a magnitude of about 100 micro Amperes ($\mu A$) to about 400 $\mu A$. In some embodiments, the electrical current output to the electrical contacts 83 may have a magnitude of about 1 mA to about 25 mA (e.g., such as in embodiments where the tool 100 is utilized to provide pacing electrical pulses to the heart 2 as described in more detail below). In some embodiments, the signal generator 85 may provide a known and desired voltage to the electrical contacts 83 (e.g., such as a desired voltage differential between the electrical contacts 83).

Sensing circuit 81 may comprise any suitable component, circuit, or collection of suitable components, circuits, etc. that are configured to detect or sense a current and/or voltage. Thus, during operations, the sensing circuit 81 may sense, measure, estimate, or otherwise detect a current or voltage at the electrical contacts 83 for a known voltage or current, respectively that was provided to the electrical contacts 83 via the signal generator 85 as previously described.

During operations, the processor 84 may output a suitable command or other signal (e.g., as a result of the machine-readable instruction 87) to the signal generator 85 to output a desired electrical current (or voltage) to one or both of the electrical contacts 83. The current (or voltage) is then conducted to the corresponding electrical contacts 120, 122 on the tool 100 via contacts 124, 126 and conductors 127, 128, respectively. The corresponding current or voltage at the electrical contacts 83 is then measured or detected via the sensing circuit 81 and is communicated to the processor 84, such that the impedance may be determined as previously described.

Referring still to FIG. 10, electronics hub 80 may also include antenna 89 that is configured to send and receive wireless signals 90 to and from, respectively, the receiver 9 as generally described above. Antenna 89 may be configured for communication with the receiver via any suitable wireless communication protocol or technology (e.g., WiFi, BLUETOOTH®, near field communications, infrared communications, etc.). In some embodiments, antenna 89 may be configured to communicate with the receiver 9 via a network (e.g., a local area network, a wide area network, etc.).

Figure 11:
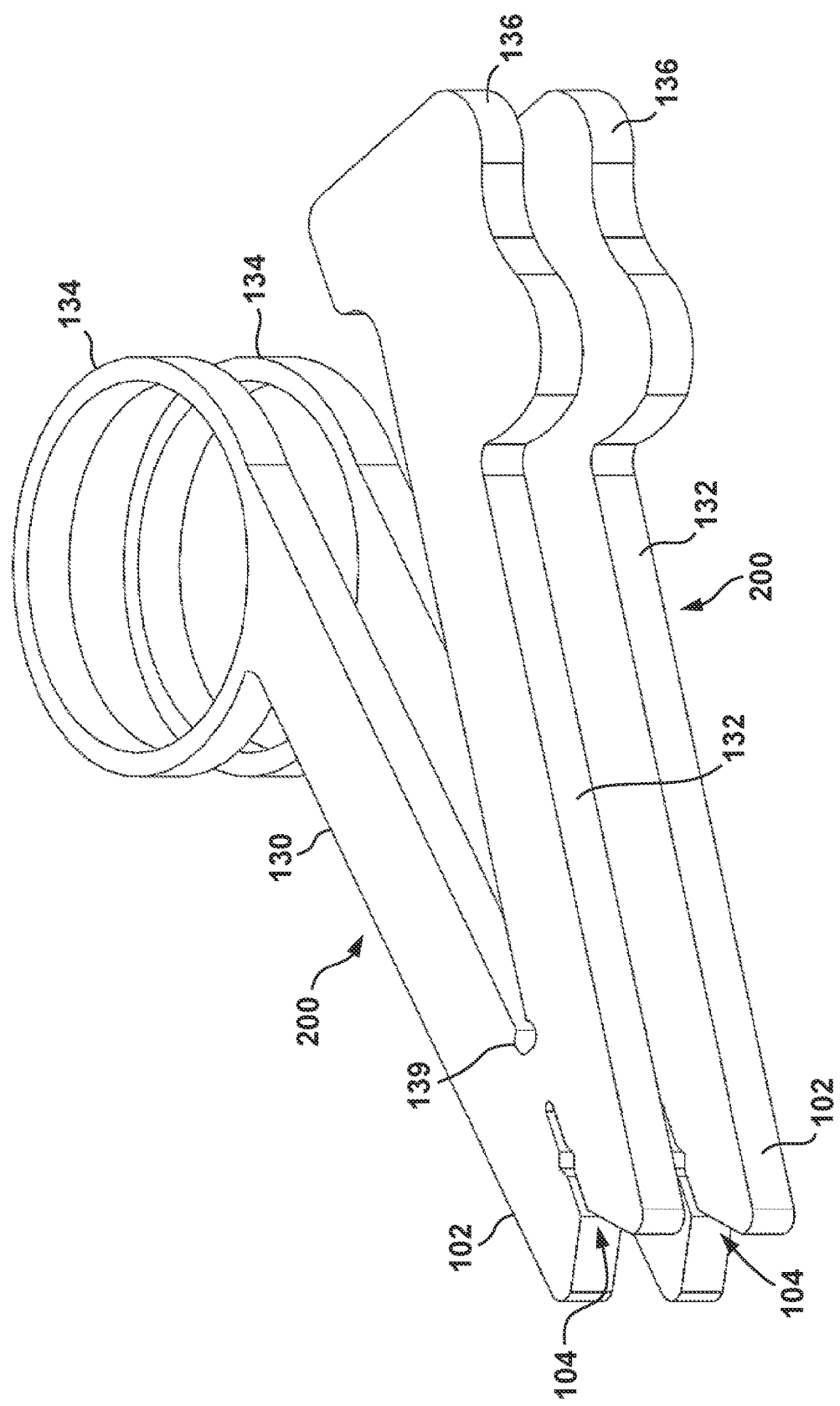
FIG. 11 is a perspective view of tools for implanting a pacemaker lead according to some embodiments.

In some embodiments multiple tools may be utilized to individually engage with the proximal-end electrodes of the pacemaker lead (e.g., electrodes 14, 18 on lead 5). For instance, reference is now made to FIG. 11 which shows a pair of tools 200 that may be utilized within the system of FIG. 1 in place or (or possibly in addition to) the tool 100. The tools 200 may be generally the same as the tool 100, and thus, components of tool 200 that are shared with the tool 100 are identified in FIG. 11 with the same reference numerals, and the description herein will focus on the features of tools 200 that are different from that described above for tool 100. Specifically, the tools 200 may not include the projection 106 and second electrical contact 122 (FIGS. 3 and 4). In addition, the tools 200 may each include the recess 104 and first electrical contact 120 as previously described above. Thus, during operations, one proximal-end electrode of the pacemaker lead (e.g., such as the first electrode 14 of lead 5) may be inserted within the recess 104 of one of the tools 200 so as to engage with the electrical contact (e.g., first electrical contact 120—not shown) disposed within the recess 104. In addition, another proximal-end electrode of the pacemaker lead (e.g., such as the second electrode 18 of lead 5) may be inserted within the recess 104 of the other of the tools 200 so as to engage with the electrical contact (e.g., first electrical contact 120—not shown) disposed within the recess 104. The tools 200 are not otherwise coupled or engaged with each other so that, during operations and following the insertion of the electrodes of the pacemaker leads within the recesses 104 of tools 200 as described above, the tools 200 may be rotated relative to one another about the axis of the pacemaker lead (e.g., axis 15 in FIG. 2) so as to insert the lead anchoring structure (e.g., anchoring structure 26) within the target tissue as previously described above. While not specifically shown, it should be appreciated that a suitable impedance measurement unit may be electrically coupled to the electrical contact disposed in the recesses 104 of tools 200 (e.g., electronics hub 80 and/or receiver 9, etc.).

In some embodiments, the recess 104 of tool 100 (FIG. 3) may include multiple pairs of notches (e.g., notches 112, 114) to receive electrodes (e.g., electrodes 14) of a pacemaker lead therein during operations. For instance, reference is now made to FIG. 12 which shows a tool 300 that may be used in the system 10 of FIG. 1 in place of tool 100. The tool 300 may be generally the same as the tool 100, and thus, components of tool 300 that are shared with the tool 100 are identified in FIG. 12 with the same reference numerals, and the description herein will focus on the features of tool 300 that are different from that described above for tool 100.

In particular, body 102 of tool 300 includes a recess 304 in place of recess 104. The recess 304 includes the notches 112, 114 as generally described above. In addition, the recess 304 also includes another pair of notches 312, 314. The notches 312, 314 may be a different size and/or shape from the notches 112, 114 so as to engage with a different size and/or type of electrode or lead during operations. In some embodiments, the same lead electrode (e.g., electrode 14 shown in FIG. 2) may be engaged with either the notches 112, 114 or the notches 312, 314 so as to adjust an interference between the recess 304 and the electrode during operations. One or both of the notches 312, 314 may include an electrical contact that may be similar to the first electrical contact 120 previously described above.

Figure 12:
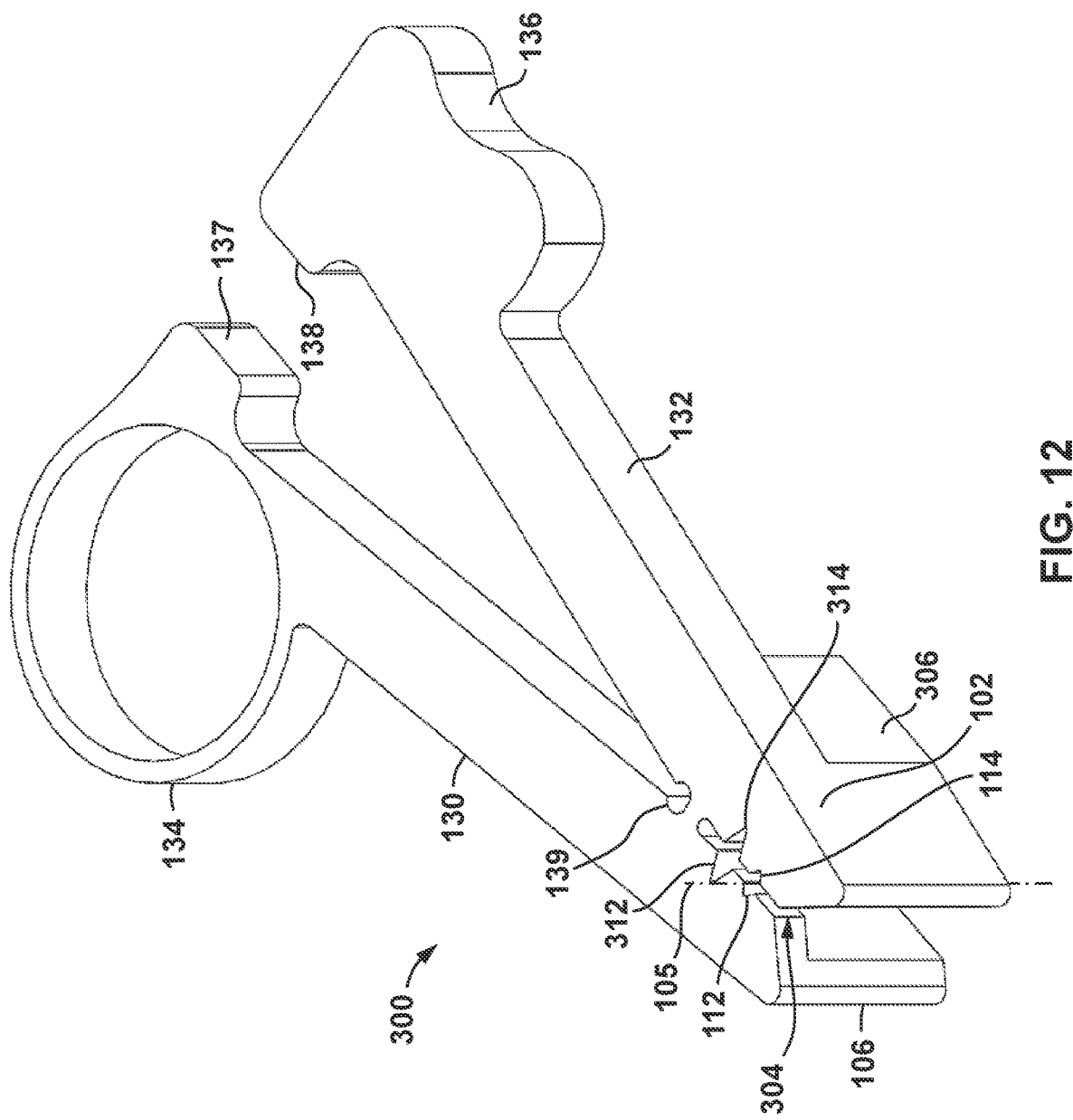
FIG. 12 is a perspective view of a tool for implanting a pacemaker lead according to some embodiments.

In addition, as is shown in FIG. 12, the tool 300 also includes a second projection 306 that is generally oppositely positioned from the projection 106 across axis 105. While not shown, the projection 306 may include an additional second electrical contact 122 (FIG. 3). Thus, during operations, multiple leads (e.g., lead 5 in FIG. 2) may be engaged with the notches 112, 114 and 312, 314 and simultaneously electrically coupled to electrical contacts disposed within the notches 112, 114, 312, 314 and on the projections 106, 306 in similar manner to that described herein. While not specifically shown, it should be appreciated that a suitable impedance measurement unit may be electrically coupled to the electrical contacts of the tool 300 (e.g., electronics hub 80 and/or receiver 9, etc.).

Figure 13:
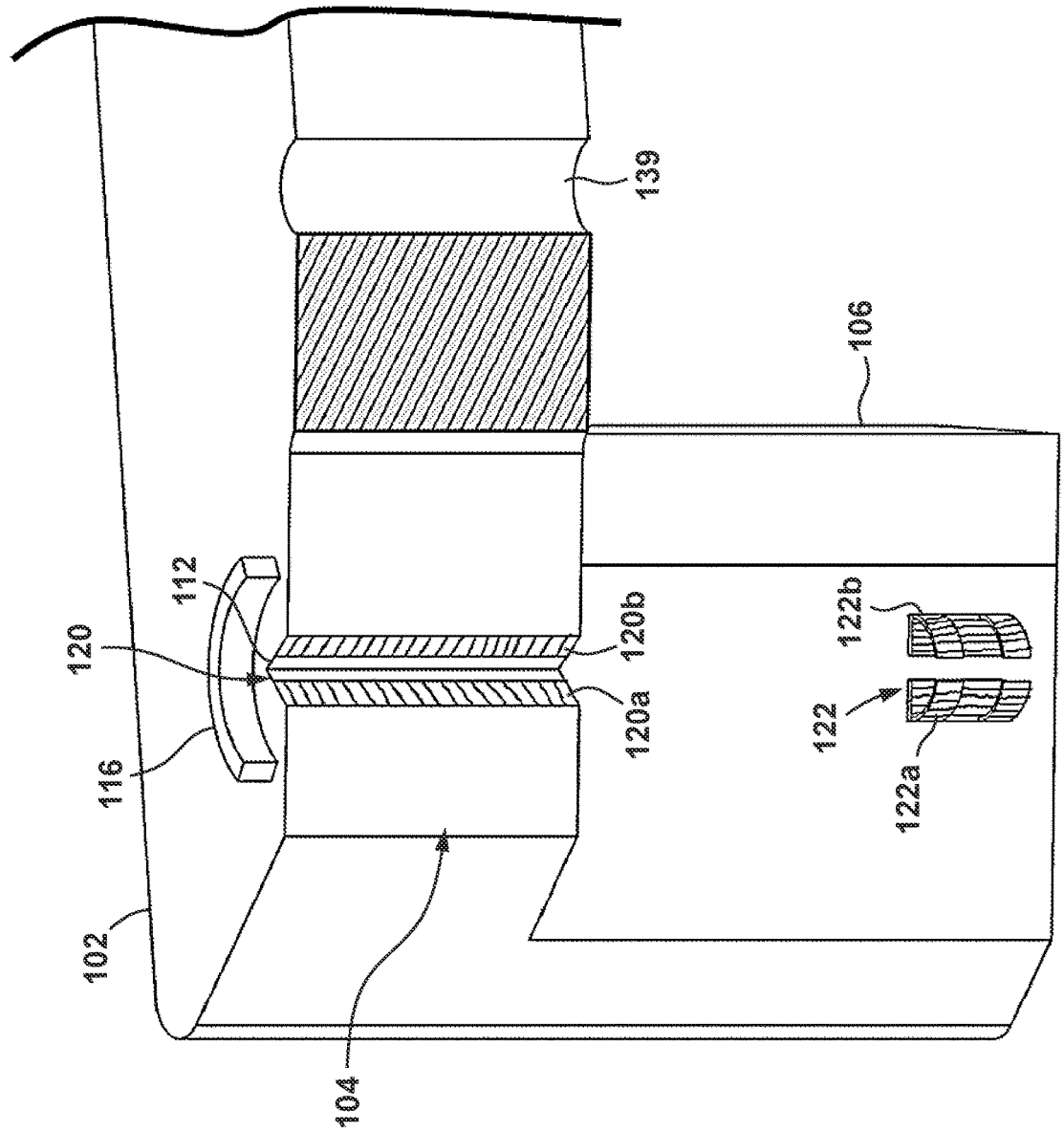
FIG. 13 is an enlarged, perspective cross-sectional view of a tool for implanting a pacemaker lead according to some embodiments.

Referring now to FIG. 13, in some embodiments, the electrical contacts 120, 122 may comprise a plurality of electrical contact surfaces. For instance, in some embodiments (e.g., such as the embodiment of FIG. 13), the first electrical contact 120 may comprise a first contact surface 120a and a second contact surface 120b, and the second electrical contact 122 may comprise a first contact surface 122a and a second contact surface 122b. The contact surfaces 120a, 120b of the first electrical contact 120 may be electrically coupled to the electronics hub 80 along a common conductor (e.g., conductor 127) or along separate electrical conductors. Similarly, the contact surfaces 122a, 122b of the second electrical contact 122 may be electrically coupled to the electronics hub 80 along a common conductor (e.g., conductor 128) or along separate electrical conductors. The contact surfaces 120a, 120b, 122a, 122b may comprise any one or more of the electrically conductive materials previously described above.

During operations, the multiple contact surfaces 120a, 120b, 122a, 122b can be utilized to provide a so-called four-way impedance monitoring functionality. Specifically, during operations, a known current or voltage may be provided to the provided to the contact surfaces 120a, 122a, and then a resulting voltage or current, respectively, can be detected at the contact surfaces 120b, 122b. By inputting and detecting the voltages and currents in this manner, error in the computed impedance resulting from the conductors (e.g., conductors 127, 128) extending between the electronics hub 80 and the electrical contacts 120, 120b, 122a, 122b may be avoided (see e.g., FIG. 6).

Referring again to FIGS. 1, 2, and 4, in some embodiments, the tool 100 may be utilized to provide electrical pulses to the myocardium via the lead 5 for purposes of pacing the contractions of the heart 2. During these operations, the electronics hub 80 may be utilized to provide a suitable electrical pulse to the electrical contact 120 that is then conducted to the myocardium via the electrode 14, conductor 16, and anchoring structure 26. As previously described above, in some embodiments, the electrical pulses may include a current of about 1 mA to about 25 mA.

Referring still to FIGS. 1, 2 and 4, in some embodiments, tool 100 may be utilized to measure or detect electrical signals within the myocardium, such as, for monitoring electrocardiogram. Specifically, during these operations, electrical signals routed within the myocardium (e.g., such as those associated with contractions of the heart 2) may be detected via the anchoring structure 26 and/or the electrode 24 and conducted, via the conductors 16, 20, to the electrodes 14, 18. These electrical signals (e.g., which may comprise a current, voltage, etc.) may then be communicated to the processor 84 of electronics 80 via electrical contacts 120, 122, conductors 127, 128, and electrical contacts 83 as previously described above so that further analysis may be conducted.

Figure 14:
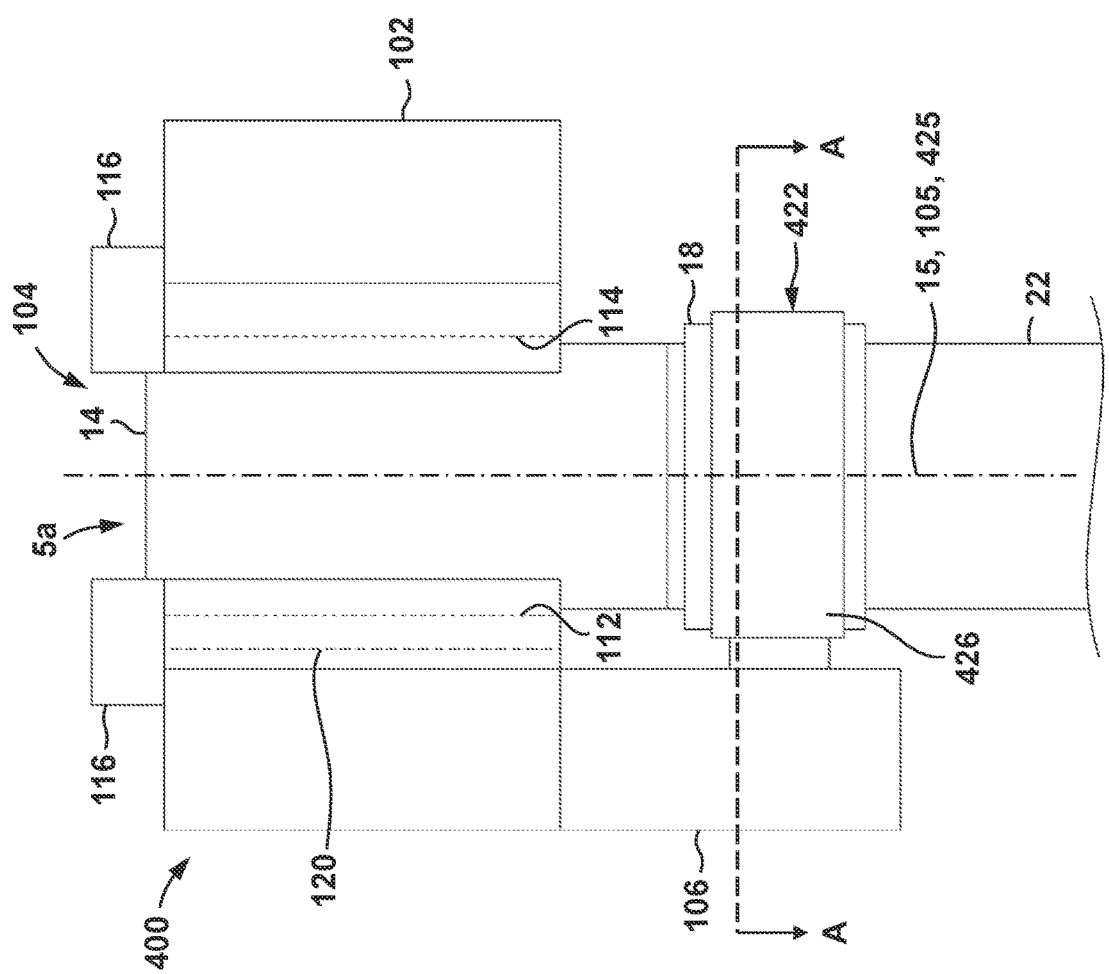
FIG. 14 is a side view of the engagement between a tool for implanting a pacemaker lead and the pacemaker lead of FIG. 2 according to some embodiments.

In some embodiments, the second electrical contact 122 may be engaged about or around the second electrode 18 of pacemaker lead 5. For instance, reference is now made to FIGS. 14 and 15 which shows a tool 400 that may be used in the system 10 of FIG. 1 in place of tool 100. The tool 400 may be generally the same as the tool 100, and thus, components of tool 400 that are shared with the tool 100 are identified in FIGS. 14 and 15 with the same reference numerals, and the description herein will focus on the features of tool 400 that are different from that described above for tool 100.

In particular, the body 102 of tool 400 includes a second electrical contact 422 in place of the second electrical contact 122 described above. The second electrical contact 422 comprises a ringed or annular member that may be circumferentially engaged about the second electrode 18 on pacemaker lead 5. The second electrical contact 422 may be electrically coupled to the electronics hub 80 (FIG. 3) in the same manner described above for second electrical contact 122.

Figure 15:
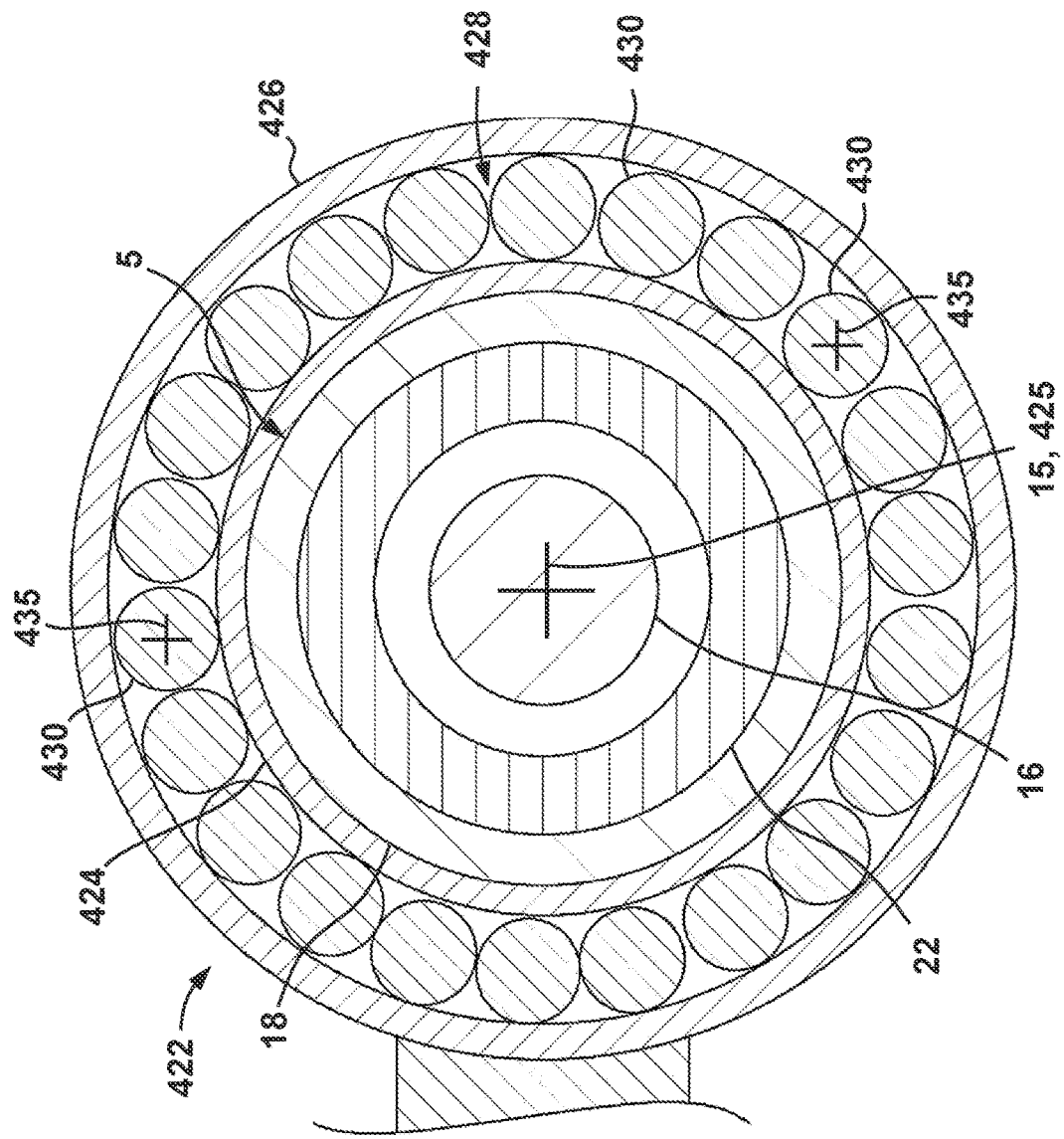
FIG. 15 is a cross-sectional view taken along section A-A in FIG. 14 according to some embodiments.

Referring specifically to FIG. 15, second electrical contact 422 includes a central or longitudinal axis 425 that may be aligned with the axis 15 of pacemaker lead 5 when the pacemaker lead 5 is engaged with the body 102 as previously described. In addition, second electrical contact 422 comprises a first or inner ring 424 and a second or outer ring 426 positioned circumferentially about the inner ring 424. A chamber 428 is defined radially between the inner ring 424 and outer ring 426 with respect to axis 425, such that the inner ring 424 may rotate freely about axis 425 relative to outer ring 426 during operations. The outer ring 426 may be fixed to projection 106 (FIG. 14) of body 102. The chamber 428 may contain a plurality of bearing elements 430 that are circumferentially arranged about axis 425. The bearing elements 430 may be spherical, cylindrical, or any other suitable shape that may allow each bearing element 430 to rotate within chamber 428 about a corresponding axis 435 that is parallel to and radially spaced from axis 425. Thus, as inner ring 424 rotates relative to outer ring 426 about axis 425, the bearing elements 430 may rotate their corresponding axes 435 and thus may also orbit circumferentially about axis 425 within the chamber 428.

Referring again to FIGS. 14 and 15, during operations pacemaker lead 5 may be inserted through inner ring 424 so that second electrode 18 is seated within inner ring 424 and first electrode 14 is engaged with first electrical contact 120 in recess 104 as previously described. Thereafter, as pacemaker lead 5 and tool 400 are rotated about axis 15 to insert or withdrawal anchoring structure 26 (FIG. 2) into the tissue of the patient 3 (FIG. 1), the inner ring 424 may rotate along with second electrode 18 within the outer ring 426 thereby avoiding tangling or twisting of second electrode 18 and sleeve 22. Thus, during operations, the second electrical contact 422 is configured to rotate about the second electrode 18 via the relative rotation of the inner ring 424 and outer ring 426.

The inner ring 424, outer ring 426, and bearing elements 430 may all be constructed from electrically conductive materials (e.g., metallic materials), so that electrical signals that are conducted to or from the second electrode 18 (and that are emitted or ultimately received by electronics hub 80 as previously described) may be conducted through the outer ring 426, bearing elements 430, and inner ring 424. In some embodiments, electrically conductive liquid may be inserted within chamber 428, between and around the bearing elements 430 so as to improve the electrical conduction between inner ring 424 and outer ring 426.

In some embodiments, the chamber 428 may not include bearing elements 428 and may instead be filled (e.g., partially, wholly) with an electrically conductive liquid. In addition, the chamber 428 may be sealed from the outer environment (e.g., at the top and bottom of the second electrode 422 to prevent dirt, dust, or other contaminants from entering chamber 428, and/or to prevent lubricant (e.g., grease, oil) or other fluids (e.g., electrically conductive liquid) from escaping the chamber 428 during operations.

Figure 16:
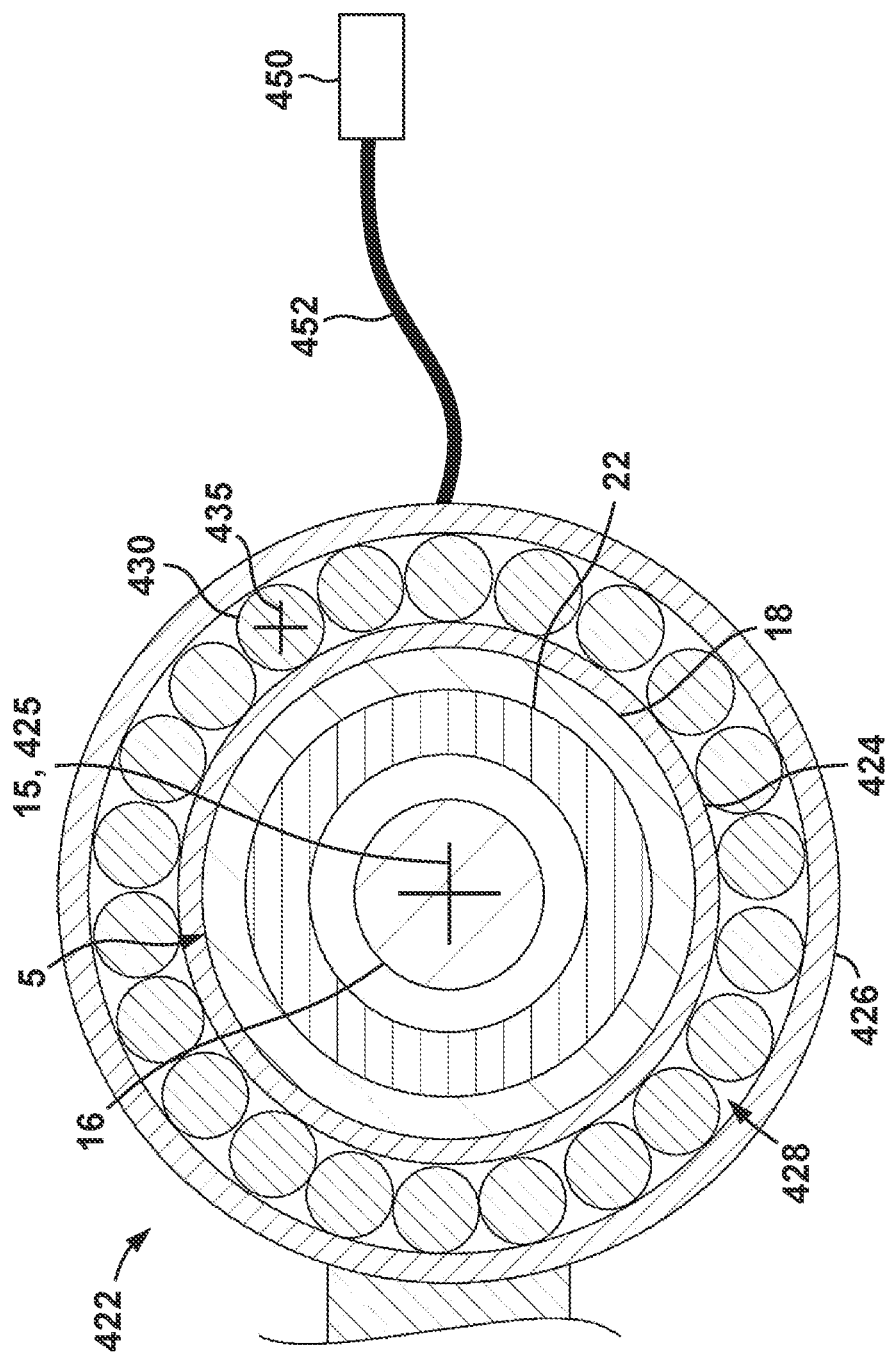
FIG. 16 is a cross-sectional view of the electrical contact of the tool of FIG. 14 coupled to an external electrode according to some embodiments.

Referring now to FIG. 16, in some embodiments, the outer ring 426 of second electrical contact 422 may be electrically coupled to an electrical contact 450 via a suitable conductor 452 (e.g., one or more wires). In addition, the outer ring 426 may be constructed of an electrically conductive material as previously described, but the inner ring 424 may be constructed and/or coated with an electrically insulating material. As a result, electrical current routed to the second electrode 18 may not be conducted to the outer ring 426 via the inner ring 424, and likewise electrical current routed to the outer ring 426 may not be conducted to the second electrode 18 via the inner ring 424.

Referring now to FIGS. 1, 2, and 16, during operations, the electrode 450 may be electrically coupled to the body of patient 3. For instance, electrode 450 may comprise (or be coupled to) an adhesive pad, an alligator clip, or any other suitable structure that may both mechanically and electrically couple the electrode 450 to the body of patient 3. Thereafter, electrical current may be applied to one of the anchoring structure 26 or the electrode 450 so that the other of the anchoring structure 26 and electrode 450 may then receive the resulting emitted current via the body of patient 3. The current conducted through the anchoring structure 26 may travel through first electrode 14, first electrical contact 120, and electronics hub 80 in the manner previously described. Likewise, electrical current routed to the electrode 450 may also travel through conductor 452, outer ring 426 and electronics hub 80 (e.g., via the conductor 128 shown in FIG. 6 as previously described). As a result, an impedance may be computed between the anchoring structure 26 and electrode 450 (e.g., via the first electrical contact 120 and second electrical contact 122 as previously described), to detect the position of the anchoring structure 26 within the myocardium (or other tissue). In addition, electrical current routed to or from the electrode 450 and anchoring structure 26 may also be used to stimulate heat tissue and/or to make other measurements (e.g., such as for a electrocardiogram as previously described).

Impedance measurements between the externally coupled electrode 450 (e.g., external to the patient 3) and the anchoring structure 26 may be referred to as "unipolar" impedance measurements. Because the electrode 450 is placed externally to the body of patient 3, the computed impedance between the first electrical contact 120 and the second electrical contact 122 may be computed through a larger area within the body of patient 3 (e.g., across the thorax of the patient 3).

In some embodiments, the electrode 450 is coupled to the inner ring 424 via a conductor (e.g., conductor 452). For instance, the electrode 450 may be coupled to a radially outer surface of the inner ring 424. The radially inner surface of the inner ring 424 may be electrically insulating (e.g., via an electrically insulating layer or coating), but at least a portion (or all) of the radially outer surface of inner ring 424 may be electrically. By making the radially inner surface of inner ring 424 electrically insulating, electrical current may not be transferred between the second electrode 18 and inner ring 424 as previously described above, and the electrically conductive outer surface of inner ring 424 may conduct electrical current from inner ring 424 to the outer ring 426 via chamber 428 as previously described (and eventually to electronics hub 80 as previously described). In addition, by coupling the electrode 450 to inner ring 424, the risk of tangling (e.g., of conductor 452) when tool 400 is rotated about axes 15, 425 may be further reduced.

Reference is now made to FIG. 17 which shows a tool 500 that may be used in the system 10 of FIG. 1 in place of tool 100. The tool 500 may be generally the same as the tool 100, and thus, components of tool 500 that are shared with the tool 100 are identified in FIG. 17 with the same reference numerals, and the description herein will focus on the features of tool 500 that are different from that described above for tool 100.

In particular, the body 102 of tool 500 includes a second electrical contact 522 in place of the second electrical contact 122 described above. The second electrical contact 522 comprises a ringed or annular member that is circumferentially engaged about the second electrode 18 on pacemaker lead 5. The second electrical contact 522 may be electrically coupled to the electronics hub 80 (FIG. 3) in the same manner described above for second electrical contact 122.

Second electrical contact 522 includes a central or longitudinal axis 525 that may be aligned with the axis 15 of pacemaker lead 5 when the pacemaker lead 5 is engaged with the body 102 as previously described and shown in FIG. 17. In addition, second electrical contact 522 comprises a ring 524 positioned circumferentially about second electrode 18 of pacemaker lead 5. The ring 524 is coupled to projection 106 via a bracket 526 that is engaged with ring 524 such that ring 524 may freely rotate about axis 525 relative to bracket 526 during operations.

Referring still to FIG. 17, during operations pacemaker lead 5 may be inserted through ring 524 so that second electrode 18 is seated within ring 524 and first electrode 14 is engaged with first electrical contact 120 in recess 104 as previously described. Thereafter, as pacemaker lead 5 and tool 400 are rotated about axis 15 to insert or withdrawal anchoring structure 26 (FIG. 2) into the tissue of the patient 3 (FIG. 1), the ring 524 may rotate along with second electrode 18 relative to bracket 526 to maintain contact with second electrode 18. Thus, during operations, the second electrical contact 522 is configured to rotate about the second electrode 18 via the rotation of the bracket 526 about the ring 524.

The ring 524 and bracket 526 may be constructed from an electrically conductive materials so that electrical current that is conducted to or from the second electrode 18 (and that are emitted or ultimately received by electronics hub 80 as previously described) may be conducted through the ring 524 and bracket 526. In some embodiments, the radially inner wall of the ring 524 may be electrically insulated or constructed from an electrically insulating material, and the radially outer wall of ring 524 may be electrically conductive or constructed from an electrically conductive material. In addition, a separate electrode (e.g., electrode 450) may be electrically coupled to the ring 524 so that unipolar impedance measurement may be obtained via the tool 500 as previously described above.

In some embodiments, the electrical contacts 422, 522 shown in FIGS. 14-17 may comprise a variety of materials. For instance, in some examples, electrical contacts 422, 522 (or portions thereof including one or more of the rings 424, 426, 524, bracket 526, or portions or surfaces of the rings 424, 426, bracket 526, etc.) may be constructed from metal, plastic, polyurethane, rubber (e.g., synthetic rubber or natural rubber), ceramics, amides, gels, or combinations thereof.

As described above, the embodiments disclosed herein include tools (e.g., tools 100, 200, 300, 400, 500, etc.) for pacemaker lead implantation that may allow for constant (or substantially constant) electrical connection with the proximal-end electrodes (e.g., electrodes 14, 18) of the lead as the anchoring structure (e.g., anchoring structure 26) of the lead is embedded into the myocardium (or other tissue). Specifically, embodiments disclosed herein may allow for constant (or substantially constant) electrical coupling of the proximal-end electrodes of the lead to a suitable impedance measurement unit during rotation of the lead to advance a helical anchoring structure within the corresponding tissue as previously described.

While exemplary embodiments have been shown and described, modifications thereof can be made by one skilled in the art without departing from the scope or teachings herein. The embodiments described herein are exemplary only and are not limiting. Many variations and modifications of the systems, apparatus, and processes described herein are possible and are within the scope of the disclosure. Accordingly, the scope of protection is not limited to the embodiments described herein, but is only limited by the claims that follow, the scope of which shall include all equivalents of the subject matter of the claims. Unless expressly stated otherwise, the steps in a method claim may be performed in any order. The recitation of identifiers such as (a), (b), (c) or (1), (2), (3) before steps in a method claim are not intended to and do not specify a particular order to the steps, but rather are used to simplify subsequent reference to such steps.

What is claimed is:

1. A tool for implanting a pacemaker lead, the tool comprising:
    a body that includes a recess;
    a first electrical contact positioned within the recess;
    a projection coupled to the body;
    a second electrical contact positioned on the projection;
    a pair of arms coupled to the body, wherein the arms are configured such that compression of the arms toward one another widens the recess; and
    an electronics hub electrically coupled to the first electrical contact and the second electrical contact, the electronics hub mounted to only one arm of the pair of arms,
    wherein the recess is configured to receive the pacemaker lead therein such that a first electrode of the pacemaker lead is to engage with the first electrical contact and a second electrode of the pacemaker lead is to engage with the second electrical contact, and
    wherein the tool is configured to rotate about a central axis of the pacemaker lead such that the first electrical contact and the first electrode rotate together about the central axis and the second electrical contact slides along the second electrode to engage with the second electrode.

2. The tool of claim 1, wherein the pair of arms is monolithically formed with the body.

3. The tool of claim 1, wherein each arm of the pair of arms comprises a first end coupled to the body and a second end spaced from the body, and wherein the body comprises an arcuate recess positioned at an intersection of the first ends of the pair of arms and the body.

4. The tool of claim 1, wherein the electronics hub comprises a processor that is configured to determine an impedance between the first electrical contact and the second electrical contact.

5. The tool of claim 4, wherein the electronics hub includes an antenna that is configured to wirelessly communicate with an electronic device.

6. The tool of claim 1, wherein the second electrical contact comprises a biasing member that is biased into engagement with the second electrode.

7. The tool of claim 1, wherein the recess comprises an inner wall, wherein the first electrical contact is embedded within the wall and defines a notch that is to engage with the first electrode of the pacemaker lead.

8. A tool for implanting a pacemaker lead, wherein the pacemaker lead includes a proximal end and a distal end, a tip electrode at the proximal end, a ring electrode at the proximal end, and an anchoring structure at the distal end, the tool comprising:
   a body that includes a central axis and a recess extending radially into the body relative to the central axis;
   a first electrical contact positioned within the recess, wherein the recess is configured to receive the tip electrode of the pacemaker lead therein such that the tip electrode of the pacemaker lead is to engage with the first electrical contact;
   a projection extending from the body in an axial direction with respect to the central axis; and
   a second electrical contact positioned on the projection, wherein the second electrical contact is configured to engaged with the ring electrode; and
   an electronics hub electrically coupled to the first electrical contact and the second electrical contact, the electronics hub comprising a processor that is configured to determine an impedance between the first electrical contact and the second electrical contact,
   wherein the tool is configured to rotate about the central axis such that the first electrical contact and the tip electrode rotate together about the central axis and the second electrical contact slides along the ring electrode in a circumferential direction about the central axis to engage with the ring electrode.

9. The tool of claim 8, comprising a pair of arms coupled to the body, wherein each of the arms extends away from the body in a direction that is perpendicular to a direction of the central axis, and wherein the arms are configured such that compression of the arms toward one another widens the recess.

10. The tool of claim 9, wherein the electronics hub is mounted to only one arm of the pair of arms.

11. The tool of claim 9, wherein the pair of arms is monolithically formed with the body.

12. The tool of claim 11, wherein each arm of the pair of arms comprises a first end coupled to the body and a second end spaced from the body, and wherein the body comprises an arcuate recess positioned at an intersection of the first ends of the pair of arms and the body.

13. The tool of claim 8, wherein the recess comprises an inner wall, wherein the first electrical contact is embedded within the wall and defines a notch that is to engage with the tip electrode of the pacemaker lead.

14. The tool of claim 8, wherein the second electrical contact comprises a leaf spring that is biased into engagement with the ring electrode.

15. A tool for implanting a pacemaker lead, the tool comprising:
   a body that includes a central axis and a recess extending radially into the body relative to the central axis;
   a pair of arms coupled to the body, the arms configured such that compression of the arms toward one another widens the recess;
   a first electrical contact including a notch that is positioned within the recess;
   a projection coupled to the body; and
   a second electrical contact positioned on the projection, the second electrical contact comprising an inner ring and an outer ring circumferentially positioned about the inner ring, the inner ring configured to rotate relative to the outer ring,
   wherein the recess is configured to receive the pacemaker lead within the notch such that a first electrode of the pacemaker lead is to engage with the first electrical contact and a second electrode of the pacemaker lead is to engage with the second electrical contact, and
   wherein the tool is configured to rotate about the central axis such that the first electrical contact and the first electrode rotate together about the central axis and the second electrical contact rotates about the second electrode.

16. The tool of claim 15, wherein the second electrical contact comprises a chamber positioned between the inner ring and the outer ring, and a plurality of bearing elements positioned within the chamber.

* * * * *